United States Patent
Martinez et al.

(10) Patent No.: US 10,512,406 B2
(45) Date of Patent: Dec. 24, 2019

(54) SYSTEMS AND METHODS FOR DETERMINING AN INTENSITY LEVEL OF AN EXERCISE USING PHOTOPLETHYSMOGRAM (PPG)

(71) Applicant: Apple Inc., Cupertino, CA (US)

(72) Inventors: Paul A. Martinez, Morgan Hill, CA (US); Tim P. D'Angelo, San Jose, CA (US); Justin P. Dobson, Sunnyvale, CA (US); Kevin B. Jessop, Cupertino, CA (US); Jose A. Castillo, San Jose, CA (US)

(73) Assignee: Apple Inc., Cupertino, CA (US)

( * ) Notice: Subject to any disclaimer, the term of this patent is extended or adjusted under 35 U.S.C. 154(b) by 158 days.

(21) Appl. No.: 15/692,736

(22) Filed: Aug. 31, 2017

(65) Prior Publication Data
US 2018/0055375 A1 Mar. 1, 2018

Related U.S. Application Data

(60) Provisional application No. 62/382,576, filed on Sep. 1, 2016.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0245* (2013.01); *A61B 5/0402* (2013.01);
(Continued)

(58) Field of Classification Search
CPC ... A61B 5/02416; A61B 5/1118; A61B 5/721; A61B 5/0245; A61B 5/7278
(Continued)

(56) References Cited

U.S. PATENT DOCUMENTS

| 4,566,461 A | 1/1986 | Lubell et al. |
| 5,158,093 A | 10/1992 | Shvartz et al. |

(Continued)

FOREIGN PATENT DOCUMENTS

| GB | 2465824 | 6/2010 |
| IN | 259/KOL/2015 | 12/2015 |

(Continued)

OTHER PUBLICATIONS

Yamaji, et al., "Relationship Between Heart Rate and Relative Oxygen Intake in Male Subjects Aged 10 to 27 Years", J. Human Ergol., 7:29-39, Jan. 27, 1978.
(Continued)

*Primary Examiner* — Amanda K Hulbert
*Assistant Examiner* — Philip C Edwards
(74) *Attorney, Agent, or Firm* — DLA Piper LLP US

(57) ABSTRACT

Disclosed systems and methods relate to determining an intensity level of an exercise using a photoplethysmogram (PPG) sensor. A method of determining an intensity level of an exercise for a user according to one embodiment of the present disclosure includes detecting, by a device, body signals from the user using a PPG sensor. The method includes determining, by the device, a heart rate of the user based on the body signals. The method includes determining, by the device, an error in the heart rate. The method also includes determining, by the device, the intensity level of the exercise for the user based at least on the error.

13 Claims, 34 Drawing Sheets

(51) Int. Cl.
  *A61B 5/11* (2006.01)
  *A61B 5/0245* (2006.01)
  *A61B 5/0402* (2006.01)
  *A61B 5/024* (2006.01)

(52) U.S. Cl.
  CPC .............. *A61B 5/11* (2013.01); *A61B 5/681* (2013.01); *A61B 5/7278* (2013.01); *A61B 5/742* (2013.01); *A61B 5/02427* (2013.01); *A61B 5/6823* (2013.01); *A61B 2562/0219* (2013.01); *A61B 2562/0223* (2013.01); *A61B 2562/0247* (2013.01)

(58) Field of Classification Search
  USPC ....................................................... 600/513
  See application file for complete search history.

(56) References Cited

U.S. PATENT DOCUMENTS

| | | |
|---|---|---|
| 5,663,897 A | 9/1997 | Geiser |
| 6,013,008 A | 1/2000 | Fukushima |
| 6,059,724 A | 5/2000 | Campell et al. |
| 6,582,380 B2 | 6/2003 | Kazlausky et al. |
| 6,687,535 B2 | 2/2004 | Hautala et al. |
| 6,837,827 B1 | 1/2005 | Lee et al. |
| 7,254,516 B2 | 8/2007 | Case, Jr. et al. |
| 7,311,675 B2 | 12/2007 | Peifer et al. |
| 7,467,060 B2 | 12/2008 | Kulach et al. |
| 7,534,206 B1 | 5/2009 | Lovitt et al. |
| 7,690,556 B1 | 4/2010 | Kahn et al. |
| 7,771,320 B2 | 8/2010 | Riley et al. |
| 7,805,149 B2 | 9/2010 | Werner et al. |
| 7,841,967 B1 | 11/2010 | Kahn et al. |
| 8,290,480 B2 | 10/2012 | Abramson et al. |
| 8,483,775 B2 | 7/2013 | Buck et al. |
| 8,589,174 B2 | 11/2013 | Nelson et al. |
| 8,892,391 B2 | 11/2014 | Tu et al. |
| 8,894,576 B2 | 11/2014 | Alwan et al. |
| 8,911,329 B2 | 12/2014 | Lin et al. |
| 9,413,871 B2 | 8/2016 | Nixon et al. |
| 9,526,430 B2 | 12/2016 | Srinivas et al. |
| 9,788,794 B2 | 10/2017 | Le Boeuf et al. |
| 10,188,347 B2 | 1/2019 | Self et al. |
| 10,206,627 B2 | 2/2019 | Le Boeuf et al. |
| 10,219,708 B2 | 3/2019 | Altini |
| 10,292,606 B2 | 5/2019 | Wisbey et al. |
| 2001/0022828 A1 | 9/2001 | Pyles |
| 2002/0019585 A1 | 2/2002 | Dickinson |
| 2003/0032460 A1 | 2/2003 | Cannon et al. |
| 2004/0064061 A1 | 4/2004 | Nissila |
| 2005/0107723 A1 | 5/2005 | Wehman et al. |
| 2006/0136173 A1 | 6/2006 | Case et al. |
| 2006/0190217 A1 | 8/2006 | Lee et al. |
| 2006/0217231 A1 | 9/2006 | Parks et al. |
| 2007/0100666 A1 | 5/2007 | Stivoric et al. |
| 2007/0150229 A1 | 6/2007 | Fujiwara |
| 2007/0219059 A1 | 9/2007 | Schwartz et al. |
| 2007/0275825 A1 | 11/2007 | O'Brien |
| 2007/0276271 A1 | 11/2007 | Chan |
| 2008/0096726 A1 | 4/2008 | Riley et al. |
| 2008/0214360 A1 | 9/2008 | Stirling et al. |
| 2009/0009320 A1 | 1/2009 | O'Connor et al. |
| 2009/0024332 A1 | 1/2009 | Karlov et al. |
| 2009/0043531 A1 | 2/2009 | Kahn et al. |
| 2009/0063099 A1 | 3/2009 | Counts et al. |
| 2010/0030350 A1 | 2/2010 | House et al. |
| 2010/0130890 A1 | 5/2010 | Matsumura et al. |
| 2010/0184564 A1 | 7/2010 | Molyneux et al. |
| 2010/0204952 A1 | 8/2010 | Irlam et al. |
| 2010/0210953 A1 | 8/2010 | Sholder et al. |
| 2010/0210975 A1 | 8/2010 | Anthony, III et al. |
| 2010/0217099 A1 | 8/2010 | Leboeuf et al. |
| 2010/0274102 A1 | 10/2010 | Teixeira |
| 2010/0298656 A1 | 11/2010 | Mccombie et al. |
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1 | 12/2011 | Teixeira |
| 2012/0083715 A1 | 4/2012 | Yuen et al. |
| 2012/0172677 A1 | 7/2012 | Logan et al. |
| 2012/0238832 A1 | 9/2012 | Jang et al. |
| 2012/0296455 A1 | 11/2012 | Ohnemus et al. |
| 2012/0322621 A1 | 12/2012 | Bingham et al. |
| 2013/0023739 A1 | 1/2013 | Russel |
| 2013/0041590 A1 | 2/2013 | Burich et al. |
| 2013/0053990 A1 | 2/2013 | Ackland |
| 2013/0096943 A1 | 4/2013 | Carey et al. |
| 2013/0158686 A1 | 6/2013 | Zhang et al. |
| 2013/0178335 A1 | 7/2013 | Lin et al. |
| 2013/0197377 A1 | 8/2013 | Takahiko et al. |
| 2013/0218053 A1 | 8/2013 | Kaiser et al. |
| 2013/0267794 A1 | 10/2013 | Fernstrom et al. |
| 2014/0073486 A1* | 3/2014 | Ahmed .............. A61B 5/02405 482/9 |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0167973 A1 | 6/2014 | Letchner et al. |
| 2014/0172238 A1 | 6/2014 | Craine |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1 | 7/2014 | Lee et al. |
| 2014/0221854 A1 | 8/2014 | Wai |
| 2014/0228649 A1* | 8/2014 | Rayner ................ A61B 5/1118 600/301 |
| 2014/0244071 A1 | 8/2014 | Czaja et al. |
| 2014/0266789 A1 | 9/2014 | Matus |
| 2014/0276127 A1 | 9/2014 | Ferdosi et al. |
| 2014/0278139 A1 | 9/2014 | Hong et al. |
| 2014/0278229 A1 | 9/2014 | Hong et al. |
| 2014/0316305 A1 | 10/2014 | Venkatraman et al. |
| 2014/0348367 A1 | 11/2014 | Vavrus et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0119728 A1 | 4/2015 | Blackadar et al. |
| 2015/0148632 A1 | 5/2015 | Benaron |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0327804 A1 | 11/2015 | Lefever et al. |
| 2015/0328523 A1 | 11/2015 | Heling et al. |
| 2015/0338926 A1 | 11/2015 | Park et al. |
| 2015/0345985 A1 | 12/2015 | Fung et al. |
| 2015/0374240 A1 | 12/2015 | Lee |
| 2016/0021238 A1 | 1/2016 | Abramson et al. |
| 2016/0057372 A1 | 3/2016 | Raghuram et al. |
| 2016/0058302 A1 | 3/2016 | Raghuram et al. |
| 2016/0058329 A1 | 3/2016 | Srinivas |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0059079 A1 | 3/2016 | Watterson |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0256058 A1 | 9/2016 | Pham et al. |
| 2016/0269572 A1 | 9/2016 | Erkkila et al. |
| 2016/0287177 A1 | 10/2016 | Huppert et al. |
| 2016/0361020 A1 | 12/2016 | LeBoeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roover et al. |
| 2017/0074897 A1 | 3/2017 | Mermel et al. |

(56) References Cited

U.S. PATENT DOCUMENTS

| | | | |
|---|---|---|---|
| 2017/0082649 | A1 | 3/2017 | Tu et al. |
| 2017/0094450 | A1 | 3/2017 | Tu et al. |
| 2017/0111768 | A1 | 4/2017 | Smith et al. |
| 2017/0188893 | A1 | 7/2017 | Venkatraman et al. |
| 2017/0202486 | A1 | 7/2017 | Marlikka et al. |
| 2017/0251972 | A1 | 9/2017 | Jayaraman et al. |
| 2017/0259116 | A1 | 9/2017 | Mestas |
| 2017/0273619 | A1 | 9/2017 | Alvarado et al. |
| 2017/0347885 | A1 | 12/2017 | Tan et al. |
| 2017/0367658 | A1 | 12/2017 | LeBoeuf et al. |
| 2018/0049694 | A1 | 2/2018 | Singh Alvarado et al. |
| 2018/0050235 | A1 | 2/2018 | Tan et al. |
| 2018/0055439 | A1 | 3/2018 | Pham et al. |
| 2018/0056123 | A1 | 3/2018 | Narasimha Rao et al. |
| 2018/0056128 | A1 | 3/2018 | Narasimha Rao et al. |
| 2018/0056129 | A1 | 3/2018 | Narasimha Rao et al. |

FOREIGN PATENT DOCUMENTS

| | | |
|---|---|---|
| WO | 2010090867 | 8/2010 |
| WO | 2011/105914 A1 | 9/2011 |
| WO | 2015/200900 A1 | 12/2015 |
| WO | 2016/044831 A1 | 3/2016 |
| WO | 2016/073620 A1 | 5/2016 |

OTHER PUBLICATIONS

Novatel, "IMU Error and Their Effects", Novatel Application Notes APN-064 Rev A p. 1-6, Feb. 21, 2014.

Your Fitness FAQ, Why is it important to warm up and cool down in a workout?, 2012, Web, Retrieved from: http://www.yourfitnessfaq.com/whyisitimportanttowarmupandcooldowninaworkout.html.

Vella et al, Exercise After-Burn: Research Update, 2005, Web, Retrieved from: http://www.unm.edu/~lkravitz/Article/020folder/epocarticle.html.

Song et al., "Training Activity Recognition Systems Online Using Real-Time Crowdsourcing", University of Rochester Computer Science, UbiCom' 12, Sep. 5-8, 2012 (2 pages).

Rowlands et al., "Assessing Sedentary Behavior with the GENEActiv: Introducing the Sedentary Sphere". Medicine and science in sports and exercise 46.6 (2014): 1235-1247.

Hasson et al., "Accuracy of four resting metabolic rate production equations: Effects of sex, body mass index, age, and race/ethnicity", Journal of Science and Medicine in Sport, 2011, vol. 14, p. 344-351.

Lucas et al., "Mechanisms of orthostatic intolerance following very prolonged exercise", 2008, J Appl Physiol, 105: 213-225.

Kunze et al., "Where am i: Recognizing on-body positions of wearable sensors." Location-and context-awareness. Springer Berlin Heidelberg, 2005. 264-275.

Keytel et al., "Prediction of energy expenditure from heart rate monitoring during submaximal exercise", 2005, Journal of Sports Sciences, 23(3):289-97.

Sabatini, Kalman-filter orientation determination using inertial/magnetic sensors: observability analysis and performance evaluation, Sep. 27, 2011, Sensors 2011, 11, 9182-9206.

Jackson et al., "Prediction of functional aerobic capacity without exercise testing", Medicine and Science in Sports and Exercise, 22(6), 863-870, 1990.

Isaacs et al., "Modeling energy expenditure and oxygen consumption in human exposure models: accounting for fatigue and EPOC", 2008, Journal of Exposure Science and Environmental Epidemiology, 18: 289-298.

Human Kinetics, Aerobic Workout Components, 2011, Web, Retrieved from: http://www.humankinetics.com/excerpts/excerpts/aerobicworkoutcomponentsexcerpt.

Gao et al., "Evaluation of accelerometer based multi-sensor versus single-sensor activity recognition systems." Medical engineering & physics 36.6 (2014): 779-785.

Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.

Chu, "In-Vehicle Driver Detection Using Mobile Phone Sensors", Submitted for Graduation with departmental Distinction in Electrical and Computer Engineering, April 20, 2011, pp. 1-21.

Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).

Bruce, R.A. et al., "Exercising testing in adult normal subjects and cardiac patients," Pediatrics, vol. 32, No. Suppl., pp. 742-756 (Oct. 1963).

Bruce, R.A. et al., "Maximal oxygen intake and nomographic assessment of functional aerobic impairment in cardiovascular disease," American Heart Journal, vol. 85, Issue 4, pp. 546-562 (Apr. 1973).

Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Cavanagh, P.R. et al., "The effect of stride length variation on oxygen uptake during distance running," Medicine and Science in Sports and Exercise, vol. 14, No. 1, pp. 30-35 (1982).

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

Fox, S.M. et al., "Physical Activity and the Prevention of Coronary Heart Disease," Bull. N.Y. Acad. Med., vol. 44, No. 8, pp. 950-967 (Aug. 1968).

Glass, S., et al., "ACSM's Metabolic Calculations Handbook," Lippincott Williams & Wilkins, 124 pages (2007).

Lavie, C.J. et al., "Impact of cardiorespiratory fitness on the obesity paradox in patients with heart failure," Mayo Clinic Proceedings, vol. 88, No. 3, pp. 251-258 (Mar. 2013).

Margaria, R. et al., "Energy cost of running," Journal of Applied Physiology, vol. 18, No. 2, pp. 367-370 (Mar. 1, 1963).

McArdle, W.D. et al., "Exercise Physiology: Nutrition, Energy and Human Performance," Seventh Edition, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for.

Myers, J. et al., "Exercise Capacity and Mortality Among Men Referred for Exercise Testing," The New England Journal of Medicine, vol. 346, No. 11, pp. 793-801 (Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Rapoport, Benjamin I., "Metabolic Factors Limiting Performance in Marathon Runners," PLoS Computational Biology, vol. 6, Issue 10, 13 pages (Oct. 2010).

Tanaka, H. et al., "Age-predicted maximal heart rate revisited," Journal of the American College of Cardiology, vol. 37, Issue 1, pp. 153-156 (Jan. 2001).

Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).

(56) References Cited

OTHER PUBLICATIONS

International Search Report and Written Opinion received for PCT Patent Application No. PCT/US2018/047290, dated Nov. 8, 2018, 14 pages.
KINprof, May 31, 2011, Predictive VO2max tests, Web Video, Retrieved from: https://www.youtube.com/watch?v=_9e3HcY1sm8.
PCT International Application No. PCT/US2017/049693, International Search Report dated Aug. 12, 2017, 3 pages.
Le, et al., "Sensor-based Training Optimization of a Cyclist Group", Seventh International Conference on Hybrid Intelligent Systems, IEEE 2007, pp. 265-270.
Kyle, Chester R., "Reduction of Wind Resistance and Power Output of Racing Cyclists and Runners Travelling in Groups", Ergonomics, vol. 22, No. 4, 1979, pp. 387-397.

* cited by examiner

SYSTEMS AND METHODS FOR DETERMINING AN INTENSITY LEVEL OF AN EXERCISE USING PHOTOPLETHYSMOGRAM (PPG)

CROSS-REFERENCE TO RELATED APPLICATION

This application claims priority of and the benefit of U.S. Provisional Application No. 62/382,576, titled "System and methods for determining an intensity level of an exercise using photoplethysmogram (PPG)", which was filed on Sep. 1, 2016 and is incorporated by reference herein in its entirety.

FIELD

The present disclosure relates to determining an intensity level of an exercise using a photoplethysmogram (PPG) sensor.

BACKGROUND

A heart rate can be measured using various mechanisms, including electrocardiogram (ECG) and photoplethysmogram (PPG). ECG sensors use electrical activity of a heart to measure the heart rate. PPG sensors use an optical technology to measure the rate of blood flow and derive the heart rate.

A person's heart rate can be measured using ECG or PPG while the person performs an exercise. The person can exercise at various intensity levels. Generally, the higher the intensity level, the higher the heart rate becomes. The person can benefit by knowing the intensity level at which the person exercises. Accordingly, it is desirable to provide methods and systems of determining the intensity level for a person performing an exercise.

SUMMARY

The present disclosure relates to a method for improving an accuracy of a wearable device while calculating an intensity level of an exercise for a user during an exercise session. The method can include: measuring, by a first heart rate sensor of the wearable device, a first heart rate of the user during the exercise session, wherein the first heart rate sensor can include a photoplethysmogram (PPG) sensor and the PPG sensor is configured to be worn adjacent to the user's skin; measuring, by a second heart rate sensor of a chest strap device, a second heart rate of the user during the exercise session, wherein the second heart rate sensor comprises an electrocardiogram (ECG) sensor; determining, by a processor circuit of the wearable device, an error in the first heart rate based on the measured first heart rate and the second heart rate; identifying, by the processor circuit, experimental data from a library of experimental data, wherein the identified experimental data is associated with a heart rate error similar to the determined error in the first heart rate; calculating, by the processor circuit, an intensity level of the exercise for the user based on the determined error in the first heart rate and the identified experimental data; and outputting, by the processor circuit, the determined intensity level of the exercise.

In some embodiments, the method can include determining, by the processor circuit, a similarity between shapes of a first group of curves associated with the first heart rate and the second heart rate and shapes of a second group of curves associated with the experimental data from the library of experimental data.

In some embodiments, the method can include determining the intensity level of the exercise based on at least one of the user's age, gender, or weight. In some embodiments, the method can include determining the intensity level of the exercise based on motion data received from at least one of an accelerometer, a gyroscope, or a barometer.

The present disclosure also relates to a method for improving an accuracy of a wearable device while calculating an intensity level of an exercise for a user. The method can include: detecting, by one or more motion sensors of a wearable device, one or more body movements of the user; analyzing, by a processor circuit of the wearable device, the detected one or more body movements of the user; measuring, by a heart rate sensor of the wearable device, a heart rate of the user, wherein the heart rate sensor can include a photoplethysmogram (PPG) sensor and the PPG sensor is configured to be worn adjacent to the user's skin; identifying, by the processor circuit, experimental data from a library of experimental data, wherein the identified experimental data is associated with a heart rate similar to the measured heart rate; calculating, by the processor circuit, an intensity level of the exercise based on the analysis of the detected one or more body movements, the measured heart rate and the identified experimental data; and outputting, by the processor circuit, the determined intensity level of the exercise. In some embodiments, the one or more motion sensors can include at least one of an accelerometer, a gyroscope, or a magnetometer.

In some embodiments, the method can include determining, by the processor circuit, a type of exercise that the user is performing based on the detected one or more body movements; and determining, by the processor circuit, a skill level of the user for the type of exercise that the user is performing based on the detected one or more body movements.

In some embodiments, the method can include providing, by the processor circuit, coaching information to the user based on at least one of the determined intensity level, the user's age, gender, experience level, activity level, physical condition, medical history, training history, or training goals.

In some embodiments, the library of experimental data can include a person's heart rate and exercise intensity levels associated with the heart rates. In some embodiments, the library of experimental data can include at least one of ages, genders, physical conditions, medical history, weights, heights, body mass indexes, types of exercise, duration of exercise, fitness levels, experience levels, body temperatures, external temperatures, or external humidity levels. In some embodiments, the method can include comparing a first signature of the measured heart rate to a second signature of a heart rate associated with experimental data from the library of experimental data.

In some embodiments, the first signature can include a shape of a data curve.

The present disclosure also relates to a system for improving an accuracy of a wearable device while calculating an intensity level of an exercise for a user. The system can include: one or more motion sensors configured to detect one or more body movements of the user; a heart rate sensor configured to measure a heart rate of the user, wherein the heart rate sensor can include a photoplethysmogram (PPG) sensor and the PPG sensor is configured to be worn adjacent to the user's skin; a processor circuit in communication with the one or more motion sensor and the heart rate sensor and configured to execute instructions causing the processor circuit to: analyze the detected one or more body movements of the user; compare the heart rate with a library of experimental data; identify experimental data from a library of experimental data, wherein the identified experimental data is associated with a heart rate similar to the measured heart rate; calculating an intensity level of the exercise based on the analysis of the detected one or more body movements, the measured heart rate and the identified experimental data; and output the determined intensity level of the exercise.

Other features and advantages will become apparent from the following detailed description and drawings.

BRIEF DESCRIPTION OF THE DRAWINGS

Various objects, features, and advantages of the present disclosure can be more fully appreciated with reference to the following detailed description of the present disclosure when considered in connection with the following drawings, in which like reference numerals identify like elements.

DETAILED DESCRIPTION

Figure 1:
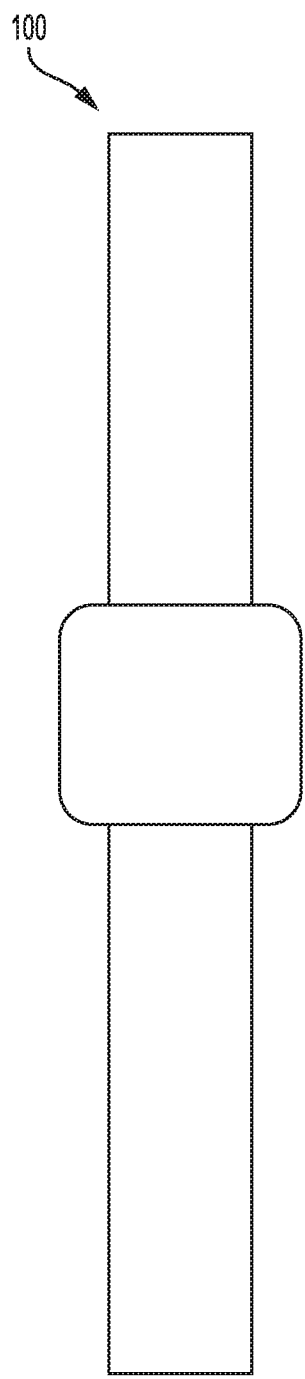
FIG. 1 shows an example of a wearable device (or a "user device") according to some embodiments of the present disclosure.

In the following description, numerous specific details are set forth regarding the systems, methods and media of the present disclosure and the environment in which such systems, methods and media may operate, etc., in order to provide a thorough understanding of the present disclosure. It will be apparent to one skilled in the art, however, that the present disclosure may be practiced without such specific details, and that certain features, which are well known in the art, are not described in detail in order to avoid complication of the present disclosure. In addition, it will be understood that the examples provided below are exemplary, and that it is contemplated that there are other systems, methods, and media that are within the scope of the present disclosure.

Electrocardiogram (ECG) provides a mechanism that can be used to determine a person's heart rate by monitoring the heart's electrical signals and measuring heartbeats over a period of time. ECG can be implemented in many different types of devices in various forms and shapes. For example, ECG sensors can be implemented in a chest strap, which a user can wear around the chest.

Photoplethysmogram (PPG) provides another mechanism that can be used to measure a person's heart rate. PPG can derive the heart rate by optically measuring changes in the person's blood flow at a specific location. PPG can be implemented in many different types of devices in various forms and shapes. For example, a PPG sensor can be implemented in a wearable device in the form of a wrist strap, which a user can wear around the wrist. The PPG sensor can optically measure the blood flow at the wrist. Based on the blood flow information, the wrist strap or another connected device can derive the person's heart rate.

Generally, ECG can determine heart rates more accurately than PPG. This is because ECG directly measures the heart rate using the heart's electric signals, whereas PPG derives the heart rate using other signals, such as changes in the blood flow. Consequently, ECG is less susceptible to external or internal interferences than PPG. Unlike ECG, the accuracy of PPG's heart rate measurements can vary depending on many conditions. Thus, the ECG-measured heart rate can be used as the reference for comparing to heart rates measured using other mechanisms, including PPG.

One of the conditions that can affect the accuracy of PPG-measured heart rate is called the "white knuckle" effect, which is related to physiologic response, where the peripheral blood is pushed out of the vasculature due to the maximal contraction of surrounding muscles. "White knuckle" describes vascular occlusion due to active muscle groups. The "white knuckle" effect can typically occur when an individual grips tightly on an object, such as a dumbbell, bicycle handle, or T-bar for rowing. One area where this effect can be easily observed is around the knuckles (interphalangeal and metacarpophalangeal joints) when performing activities requiring intense gripping. The knuckles turn white because of the lack of blood in the capillaries near the skin. The "white knuckle" effect in the context of detecting the heart rate using PPG is analogous to the same term that is used to describe a person's knuckles that whiten or turn pale when the person grips or clenches the first tightly, causing the blood to leave the hand. When the person releases the grip, the knuckles turn red again, after blood has flowed back into them. A similar "white knuckle" effect can occur in various parts of a human body, such as the tendons, ligaments, muscles and skin, when a person is engaged in an exercise, such as weight training. The "white knuckle" effect can create noise artifacts that can interfere with heart rate detection by PPG because these artifacts can limit the ability to detect the influx and outflow of blood among the various tissues being analyzed.

Moreover, the "white knuckle" effect can be observed in cardiovascular exercises, such as cycling, rowing, treadmill with hands on crossbar, elliptical, or stair master. It can also be observed in exercise routines, such as yoga and body weight exercises (e.g., pushups, burpees, etc.). These exercise routines can include exercises that are part of classes like CrossFit™. As peripheral circulation is diminished during performing these exercises, the "white knuckle" effect can be observed, and thus, the PPG sensor cannot accurately detect heart rate. The effect on the PPG sensor can also depend on where the PPG sensor is located. For example, on some areas other than the wrist on the body (e.g., forearm, forehead, and ear) that contract typically, blood flow near the skin is not affected by, for example, the "white knuckle" effect. As a result, PPG signal in these areas will not be affected.

Other scalar intensity measurements can also be used to correlate to the "white knuckle" effect. For example, heart rate recovery (and potential variation) can be compared. Other potential scalers can include EMG or maximal contractile force applied. Exercise blood pressure dynamics (specifically intrathoracic pressure) can also be considered.

During a weight training exercise, the amount of the "white knuckle" effect can be a function of the amount of weight being pushed or pulled. In some cases, this relationship can be directly proportional. When a person pushes or pulls on extremely light weight that the person is lightly gripping, the amount of the "white knuckle" effect may be either nonexistent or very small, and the blood flow in the hand remains normal or close to normal. The condition for using a PPG device on or near the hand to measure the heart rate can be optimal when the blood flow in the hand remains normal. As the amount of weight that is being pushed or pulled increases, the demands placed on the hand grip can increase in direct proportion, causing the knuckles to whiten up. As the knuckles whiten up, the accuracy in determining the heart rate by the PPG device can also decrease. In other words, the errors in PPG's heart rate measurements can be attributed to the "white knuckle" effect.

One way to measure an intensity level of an exercise is observing the amount of weight or resistance to which the person is subjected, and how heavy the person perceives that weight under tension. The intensity level can be expressed as a percentage of maximum and range from 0% to 100%. When the amount of weight being pushed or pulled is increased, the intensity level also increases. When the amount of weight being pushed or pulled is decreased, the intensity level also decreases. Even with the same amount of weight, the intensity level can vary from one person to another, and also for the same person depending on various factors. For example, performing a dumbbell military press with 60 lbs can be at 100% intensity for person X, while it can be at 50% for person Y who is more fit than person X. As another example, the same person X can perceive the same exercise at 30% intensity after spending a year in weight training. A person can benefit by knowing intensity levels while or after performing different exercises, as the person can often exercise more effectively and efficiently by adjusting the intensity levels in response. In some cases, intensity can be modeled with heart rate recovery that can describe how quickly the heart rate returns to the resting state.

There is a relationship between the amount of the "white knuckle effect" and the intensity level. The amount of the "white knuckle" effect can have a maximum point, where the knuckles can become as white as possible. At or close to this maximum point, the amount of error in PPG-measured heart rate can level off. If the person attempts to push or pull beyond this maximum point, the person would likely struggle to handle and grip the weight. This can be when the person has exceeded the point of maximum intensity.

The rate at which the knuckles turn red again after they have whitened is also a function of the gripping intensity or the intensity level of the exercise. For example, the white knuckles can take longer to return to red if the person has lifted the heavier weight. Consequently, the PPG device can take longer to measure the heart rate accurately after the user has exercised with heavy weights than had the user exercised with lighter weights.

The amount of increasing degrees of white knuckles between zero intensity and maximum intensity can be captured as the amount of increasing error that the PPG device generates when compared to the chest strap monitor that uses ECG.

The present disclosure describes a wearable device that can be configured to determine the intensity level of an exercise. In some embodiments, the wearable device can leverage experimental data created from experiments performed with a chest strap device with an ECG sensor and a wrist strap with a PPG sensor. In some embodiments, the wearable device can leverage experimental data that can show a correlation between the intensity level of an exercise and the amount of error in the PPG-measured heart rate.

FIG. 1 shows an example of a wearable device (or a "user device") 100 according to some embodiments of the present disclosure. In some embodiments, wearable device 100 may be any suitable wearable device, such as a watch and/or a fitness band configured to be worn around an individual's wrist.

Figure 2:
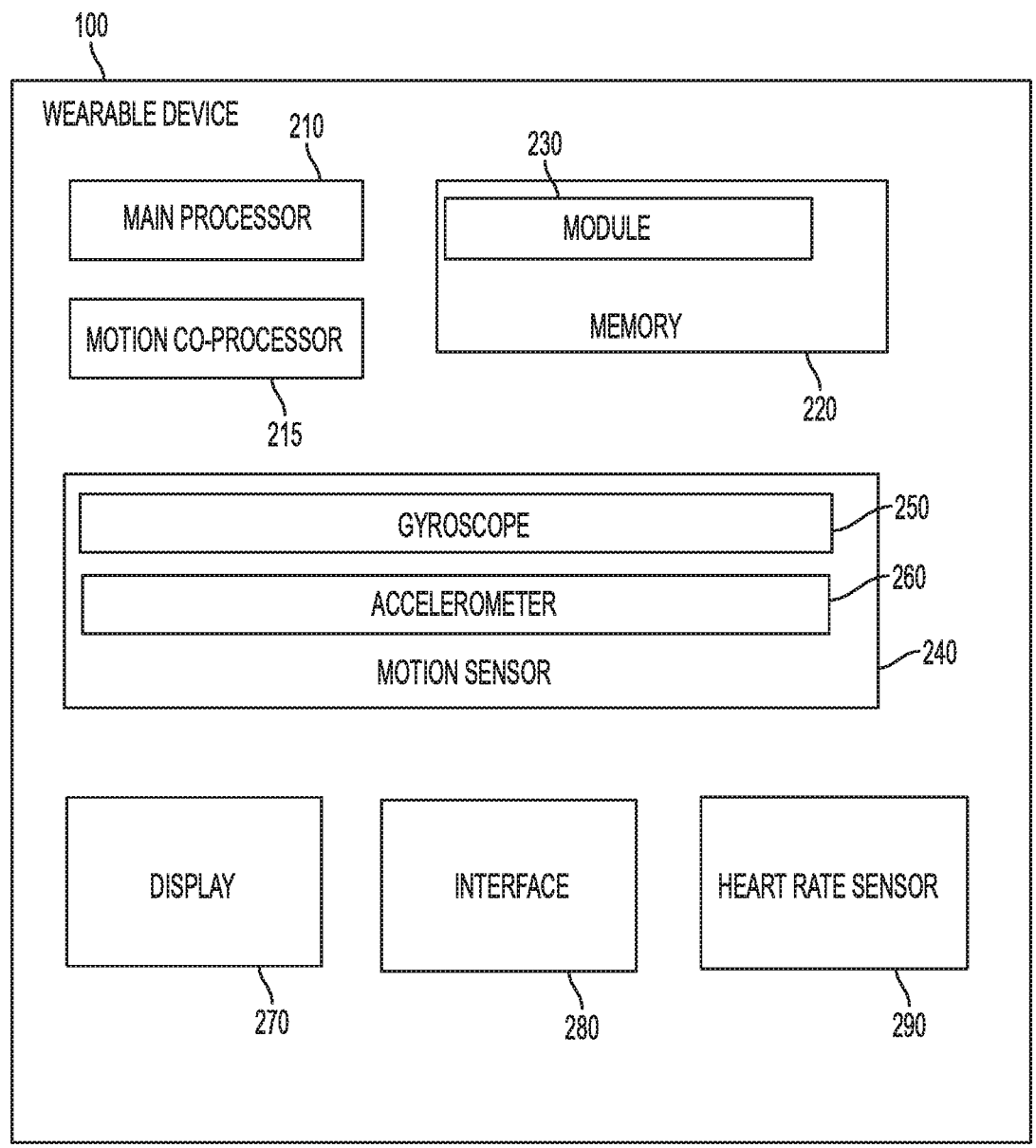
FIG. 2 depicts a block diagram of exemplary components that may be found within the wearable device according to some embodiments of the present disclosure.

FIG. 2 depicts a block diagram of exemplary components that may be found within wearable device 100 according to some embodiments of the present disclosure. Wearable device 100 can include a main processor 210 (or an "application processor"), a motion co-processor 215, a memory 220, one or more motion sensors 240, a display 270, an interface 280, and a heart rate sensor 290. Wearable device 100 may include additional modules, fewer modules, or any other suitable combination of modules that perform any suitable operation or combination of operations.

In some embodiments, main processor 210 can include one or more cores and can accommodate one or more threads to run various applications and modules. Software can run on main processor 210 capable of executing computer instructions or computer code. Main processor 210 might also be implemented in hardware using an application specific integrated circuit (ASIC), programmable logic array (PLA), field programmable gate array (FPGA), or any other integrated circuit.

In some embodiments, wearable device 100 also includes motion co-processor 215 which may draw less power than the main processor 210. Whereas the main processor 210 may be configured for general purpose computations and communications, the motion co-processor 215 may be configured to perform a relatively limited set of tasks, such as receiving and processing data from motion sensor 240, heart rate sensor 290, and other modules within the wearable device 100. In many embodiments, the main processor 210 may be powered down at certain times to conserve power, while the motion co-processor 215 remains powered on. Thus, the motion co-processor 215 is sometimes referred to as an "always-on" processor (AOP). Motion co-processor 215 may control when the main processor 210 is powered on or off.

Memory 220 can be a non-transitory computer readable medium, flash memory, a magnetic disk drive, an optical drive, a programmable read-only memory (PROM), a read-only memory (ROM), or any other memory or combination of memories. Memory 220 can include one or more modules 230.

Main processor 210 or motion co-processor 215 can be configured to run module 230 stored in memory 220 that is configured to cause main processor 210 or motion co-processor 215 to perform various steps and/or operations that are discussed throughout the present disclosure, such as, for example, the methods described in connection with FIGS. 4, 5, and 6. In some embodiments, wearable device 100 can include one or more motion sensors 240. For example, motion sensors 240 can include a gyroscope 250 and an accelerometer 260. In some embodiments, accelerometer 260 may be a three-axis accelerometer that measures linear acceleration in up to three-dimensions (for example, x-axis, y-axis, and z-axis). In some embodiments, gyroscope 250 may be a three-axis gyroscope that measures rotational data, such as rotational movement and/or angular velocity, in up to three-dimension (for example, yaw, pitch, and roll). In some embodiments, accelerometer 260 may be a microelectromechanical system (MEMS) accelerometer, and gyroscope 250 may be an MEMS gyroscope. Main processor 210 or motion co-processor 215 of wearable device 100 may receive motion information from one or more motion sensors 240 to track acceleration, rotation, position, or orientation information of wearable device 100 in six degrees of freedom through three-dimensional space.

In some embodiments, wearable device 100 may include other types of sensors in addition to accelerometer 260 and gyroscope 250. For example, wearable device 100 may include an altimeter or barometer, or other types of location sensors, such as a GPS sensor. As another example, wearable device 100 may include a light sensor. In some embodiments, sensor fusion can be implemented in wearable device 100 and/or another device for the purpose of leveraging data from various sensors in wearable device 100.

Wearable device 100 may also include display 270. Display 270 may be a screen, such as a crystalline (e.g., sapphire) or glass touchscreen, configured to provide output to the user and/or receive input from the user via touch. For example, display 270 may be configured to display a current heart rate, intensity level, and/or a daily average energy expenditure. Display 270 may receive input from the user to select, for example, which information should be displayed, or whether the user is beginning a physical activity (e.g., starting a session) or ending a physical activity (e.g., ending a session), such as weight training, swimming session, a running session, or a cycling session. In some embodiments, wearable device 100 may present output to the user in other ways, such as by producing sound with a speaker (not shown), and wearable device 100 may receive input from the user in other ways, such as by receiving voice commands via a microphone (not shown).

In some embodiments, wearable device 100 may communicate with external devices via interface 280, including a configuration to present output to a user or receive input from a user. Interface 280 may be a wireless interface. The wireless interface may be a standard Bluetooth® (IEEE 802.15) interface, such as Bluetooth® v4.0, also known as "Bluetooth® low energy." In other embodiments, the interface may operate according to a cellphone network protocol such as Long Term Evolution (LTE) or a Wi-Fi (IEEE 802.11) protocol. In other embodiments, interface 280 may include wired interfaces, such as a headphone jack or bus connector (e.g., Lightning, Thunderbolt, USB, etc.).

Wearable device 100 can measure an individual's current heart rate from heart rate sensor 290. Heart rate sensor 290 may also be configured to determine a confidence level indicating a relative likelihood of an accuracy of a given heart rate measurement. In other embodiments, a traditional heart rate monitor may be used and may communicate with wearable device 100 through a near field communication method (e.g., Bluetooth®). In some embodiments, heart rate sensor 290 includes a PPG sensor. In some embodiments, heart rate sensor 290 includes an ECG sensor.

Wearable device 100 may be configured to communicate with a companion device 300 (FIG. 3), such as a smartphone, as described in more detail herein. In some embodiments, wearable device 100 may be configured to communicate with other external devices, such as a notebook or desktop computer, tablet, headphones, Bluetooth® headset, etc.

The modules described above are examples, and embodiments of wearable device 100 may include other modules not shown. For example, some embodiments of wearable device 100 may include a rechargeable battery (e.g., a lithium-ion battery), a microphone or a microphone array, one or more cameras, one or more speakers, a watchband, water-resistant casing or coating, etc. In some embodiments, all modules within wearable device 100 can be electrically and/or mechanically coupled together. In some embodiments, main processor 210 can coordinate the communication among each module.

Figure 3:
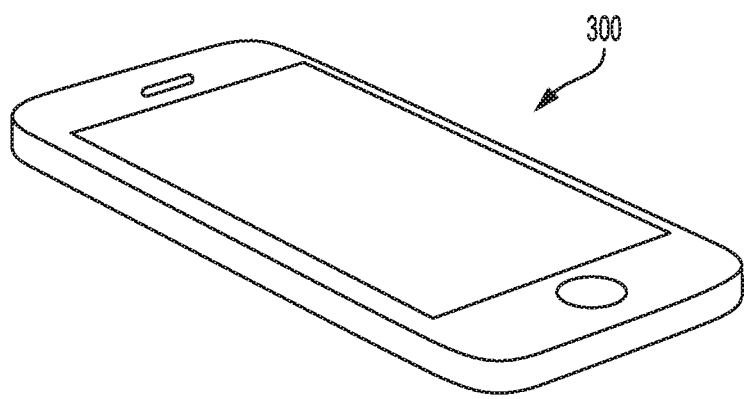
FIG. 3 shows an example of a companion device according to some embodiments of the present disclosure.

FIG. 3 shows an example of a companion device 300 according to some embodiments of the present disclosure. Wearable device 100 may be configured to communicate with companion device 300 via a wired or wireless communication channel (e.g., Bluetooth®, Wi-Fi, etc.). In some embodiments, companion device 300 may be a smartphone, tablet computer, or similar portable computing device. Companion device 300 may be carried by the user, stored in the user's pocket, strapped to the user's arm with an armband or similar device, placed in a mounting device, or otherwise positioned within communicable range of wearable device 100. In some embodiments, companion device 300 may be a personal computer, such as a desktop and a notebook, that provides less portability than a smartphone or a tablet computer.

In some embodiments, companion device 300 may include a variety of sensors, such as location and motion sensors (not shown). When companion device 300 is available for communication with wearable device 100, wearable device 100 may receive additional data from companion device 300 to improve or supplement its calibration or calorimetry processes. For example, in some embodiments, wearable device 100 may not include a GPS sensor as opposed to an alternative embodiment in which wearable device 100 may include a GPS sensor. In the case where wearable device 100 may not include a GPS sensor, a GPS sensor of companion device 300 may collect GPS location information, and wearable device 100 may receive the GPS location information via interface 280 (FIG. 2) from companion device 300.

In another example, wearable device 100 may not include an altimeter or barometer, as opposed to an alternative embodiment in which wearable device 100 may include an altimeter or barometer. In the case where wearable device 100 may not include an altimeter or barometer, an altimeter or barometer of companion device 300 may collect altitude or relative altitude information, and wearable device 100 may receive the altitude or relative altitude information via interface 280 (FIG. 2) from the companion device 300.

In another example, wearable device 100 may receive motion information from companion device 300. Wearable device 100 may compare the motion information from companion device 300 with motion information from one or more motion sensors 240 of wearable device 100. Motion information such as data from accelerometer 260 and/or gyroscope 250 may be filtered (e.g., by a high-pass, low-pass, band-pass, or band-stop filter) in order to improve the quality of motion information. For example, a low-pass filter may be used to remove some ambient noise.

Wearable device 100 may use sensed and collected motion information to predict a user's activity. Examples of activities may include, but are not limited to, weight training, walking, running, cycling, swimming, etc. Wearable device 100 may also be able to predict or otherwise detect when a user is sedentary (e.g., sleeping, sitting, standing still, driving or otherwise controlling a vehicle, etc.). Wearable device 100 may use a variety of motion information, including, in some embodiments, motion information from a companion device.

Wearable device 100 may use a variety of heuristics, algorithms, or other techniques to predict the user's activity. Wearable device 100 may also estimate a confidence level (e.g., percentage likelihood, degree of accuracy, etc.) associated with a particular prediction (e.g., 90% likelihood that the user is running) or predictions (e.g., 60% likelihood that the user is running and 40% likelihood that the user is walking).

Figure 4:
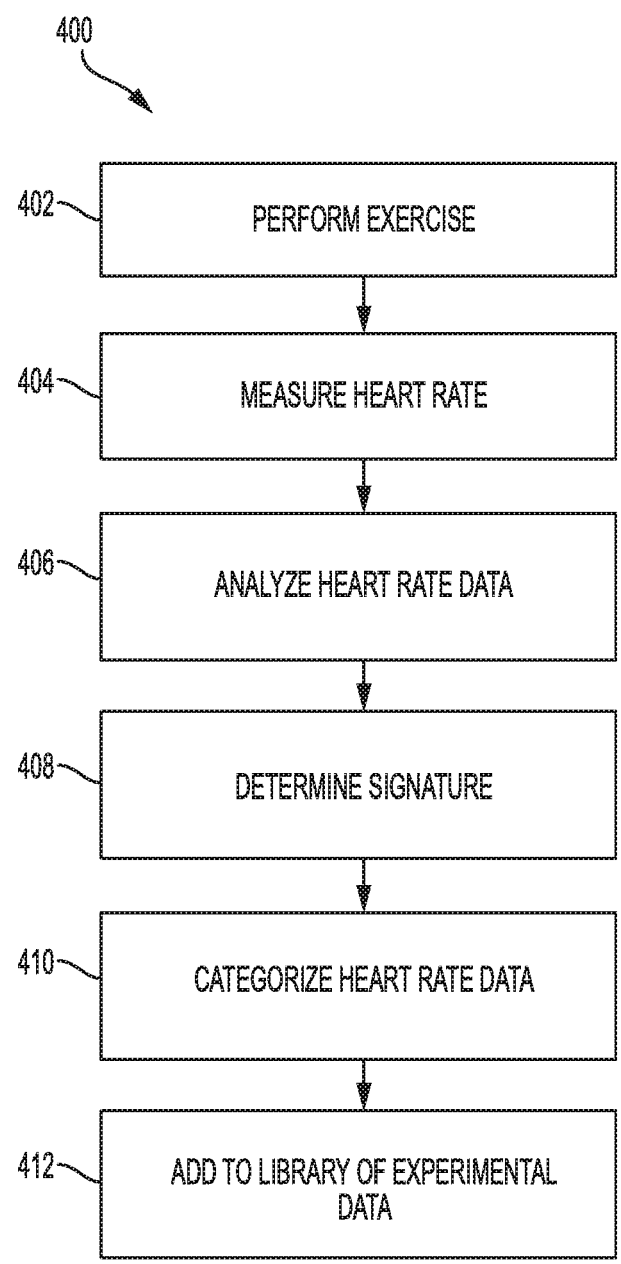
FIG. 4 illustrates a method for creating and analyzing data from experiments according to some embodiments of the present disclosure.

FIG. 4 illustrates a method 400 for creating and analyzing data from experiments according to some embodiments of the present disclosure. In some embodiments, method 400 can be modified by, for example, having blocks combined, divided, rearranged, changed, added, and/or removed. At block 402, a person subject to an experiment can perform an exercise while wearing one or more devices that can measure the person's heart rate. In some embodiments, the person can wear a device (e.g., a chest strap device) that includes an ECG sensor. In some embodiments, the person can wear another device (e.g., wearable device 100 in FIG. 1) that includes a PPG sensor. In some embodiments, one device can include both an ECG sensor and a PPG sensor.

At block 404, the device(s) that the person wears can measure the person's heart rate. For example, the chest strap device can measure the person's heart rate using the ECG sensor, while wearable device 100 can measure the person's heart rate using the PPG sensor. The heart rate measurements from different types of sensors may or may not be the same. The person's heart rate can be measured at different time intervals while performing different types of exercises.

At block 406, the measured heart rate data is analyzed. In some embodiments, the heart rate data from one person is analyzed at a time. In other embodiments, the heart rate data from more than one person can be analyzed together. For example, heart rates from two or more people can be compared, summed, and/or averaged. Statistical analysis can be performed on the heart rate data. In some embodiments, the ECG-measured heart rate is compared with the PPG-measured heart rate. For example, the difference between the ECG-measured heart rate and the PPG-measured heart rate at or at nearly the same point in time is calculated. In some embodiments, the ECG-measured heart rate can be the reference heart rate, and some or all of the difference can be attributed to an error in the PPG-measured heart rate. In some embodiments, an absolute value of this difference can be calculated. In some embodiments, this absolute value can be added to other absolute values of errors that were previously analyzed. In some embodiments, a heart rate graph can be drawn using heart rate data that has been collected from one or more persons. Examples of this graph are shown in FIGS. 7-10, 14-17, 21-24, and 28-31. Each of these heart rate graphs includes two curves—one curve for the ECG-measured heart rate and another curve for the PPG-measured heart rate. Other types of graphs, such as 11-13, 18-20, 25-27, and 32-34, can also be drawn. In some embodiments, statistical analysis can be performed on the heart rate data based on different factors, including demographic information related to the persons subject to the experiments.

At block 408, a signature can be determined for heart rate data. For example, a signature can be associated with the shape of a curve or the shape of the combination of the curves in each heart rate graph. As another example, a signature can be associated with the area between the ECG-measured heart rate curve and the PPG-measured heart rate curve. Such an area can represent the difference between the ECG-measured data and the PPG-measured data. Yet in another example, a signature can be associated with the area underneath one of the curves in the heart rate graph. Each signature can uniquely identify the origin of the data. By knowing the origin of the data, the variables and conditions that were used in the experiment can be determined.

At block 410, the heart rate data can be categorized using different criteria. For example, the heart rate data can be categorized based on the person's age, gender, physical condition, medical history, weight, height, body mass index, type of exercise, duration of exercise, fitness level, level of experience for the specific exercise performed, body temperature, external temperature, and/or external humidity level.

At block 412, the heart rate data and any related analyzed data can be stored in a library of experimental data. In some embodiments, this library can be stored in a non-volatile medium in storage that resides locally to and/or remotely from any of the above-mentioned devices. For example, the storage can reside remotely in a cloud data center, which can be accessed via the internet and/or intranet. As another example, some or all of the library data can reside in wearable device 100 and/or companion device 300.

Figure 5:
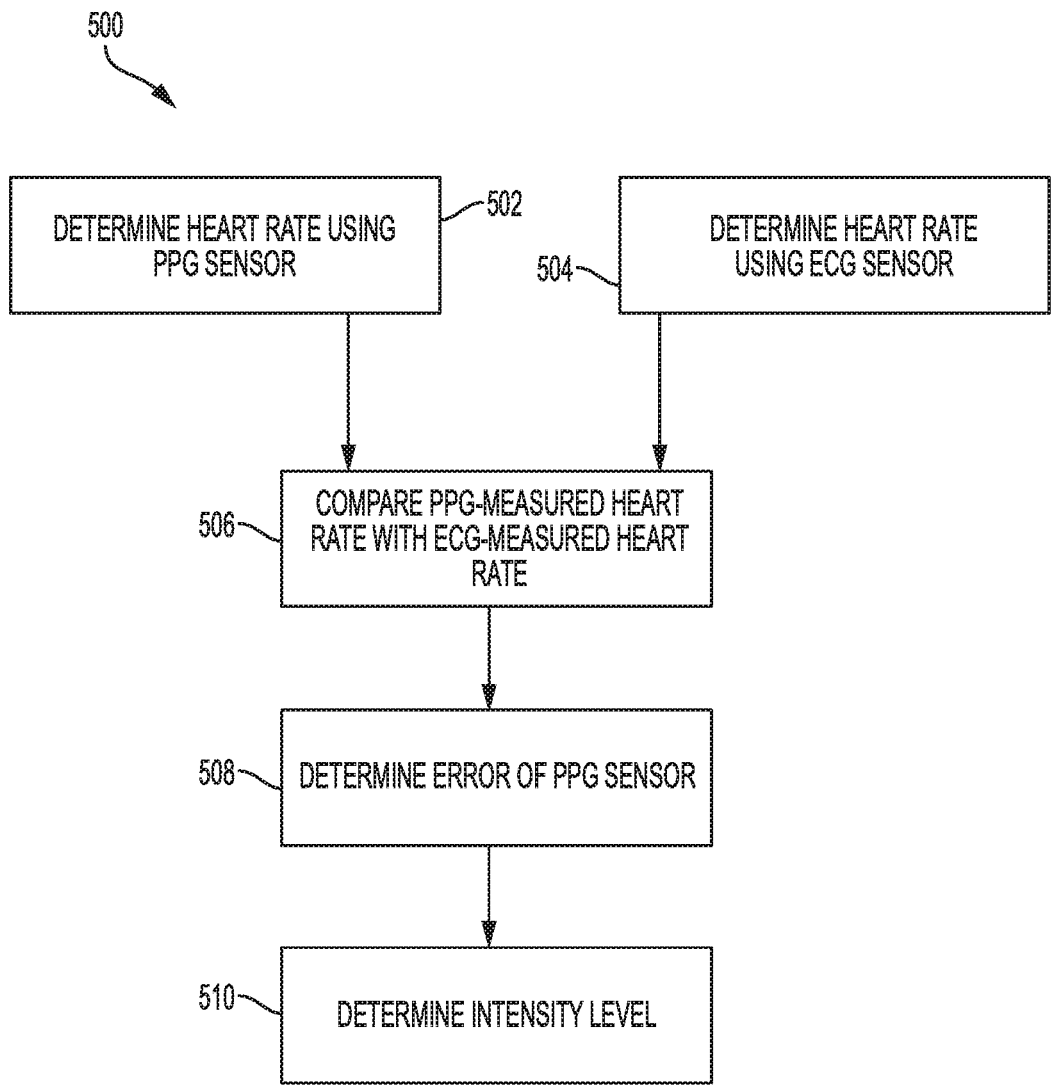
FIG. 5 illustrates a method for determining an intensity level according to some embodiments of the present disclosure.

FIG. 5 illustrates a method 500 for determining an intensity level according to some embodiments of the present disclosure. In some embodiments, method 500 can be modified by, for example, having blocks combined, divided, rearranged, changed, added, and/or removed. At block 502, a person's heart rate can be determined using a PPG sensor. For example, the person can wear wearable device 100 (FIG. 1) that includes a PPG sensor, and wearable device 100 can measure the person's heart rate. At block 504, the person's heart rate can be determined using an ECG sensor. For example, the person can wear a chest strap device with an ECG sensor. In some embodiments, the person's heart rate can be measured in block 502 and block 504 at or nearly at concurrent points in time, such that the two measurements can be compared. In some embodiments, the heart rate measured in block 502 and/or block 504 can be sent to another device (e.g., companion device 300 (FIG. 3)) for storage and/or analysis. In other embodiments, the device with the PPG sensor or the ECG sensor may not calculate the heart rate; this device may instead send raw data to another device (e.g., companion device 300) for determining the heart rate.

At block 506, the PPG-measured heart rate can be compared with the corresponding ECG-measured heart rate. There may or may not be a difference between these two heart rates. At block 508, an error in the PPG-measured heart rate can be determined. In some embodiments, the ECG-measured heart rate from block 504 can be used as the reference heart rate. If the PPG-measured heart rate from block 502 is different from the reference heart rate, some or all of this difference can be attributed to an error in the PPG-measured heart rate.

At block 510, an intensity level can be determined. For example, an exercise intensity level for a person engaged in weight training can be determined. In some embodiments, the error in the PPG-measured heart rate can be analyzed based on the library of experimental data (e.g., data from block 412 in FIG. 4). For example, the heart rate data from blocks 502 and/or 504 can be compared with experimental data to find similar data and determine the intensity level. In some embodiments, the person's information, such as person's age, gender, and weight, can be used in determining the intensity level. In some embodiments, this information can be read from HealthKit made by Apple™, Inc. (Cupertino, Calif.). In some embodiments, the accelerometer, gyroscope and/or barometer can be used to determine relative intensity level automatically. In some embodiments, the shapes of the curves drawn using the PPG-measured heart rate and the ECG-measured heart rate are compared to the curves in the library of experimental data to determine the intensity level. In some embodiments, other measures in addition to, or in place of the intensity level can be determined. For example, a level of efforts can be determined.

Figure 6:
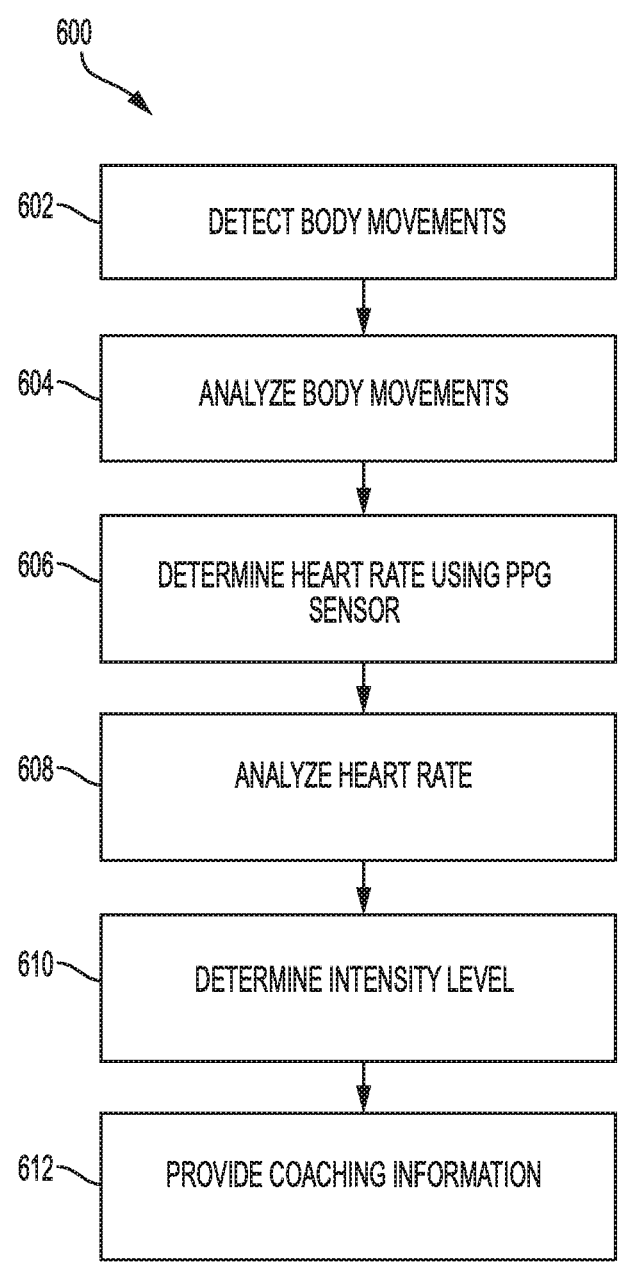
FIG. 6 illustrates a method for determining and utilizing an intensity level according to some embodiments of the present disclosure.
Figure 7:
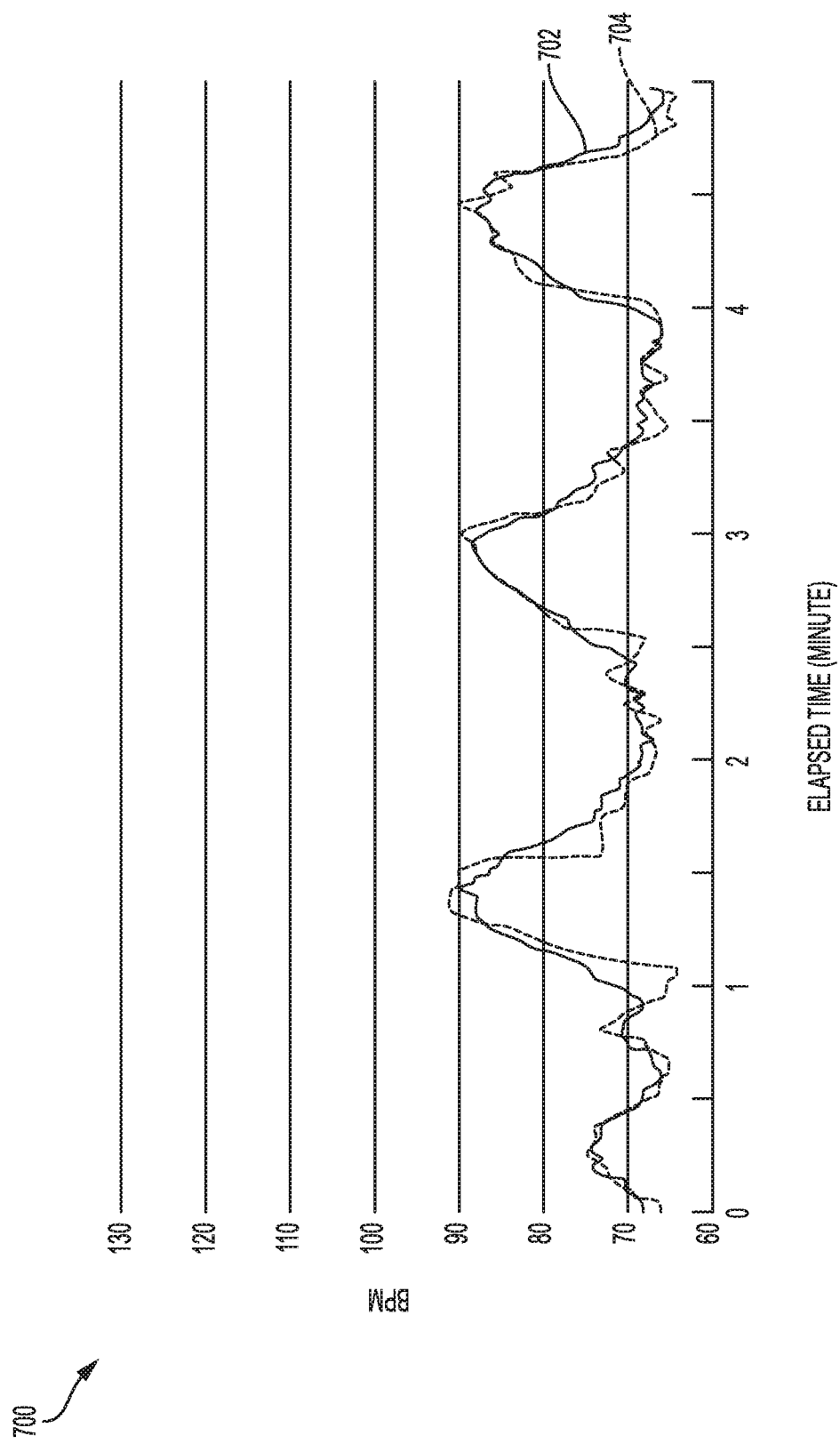
FIGS. 7-13 show graphs drawn using experimental data associated with performing a bench press exercise.
Figure 8:
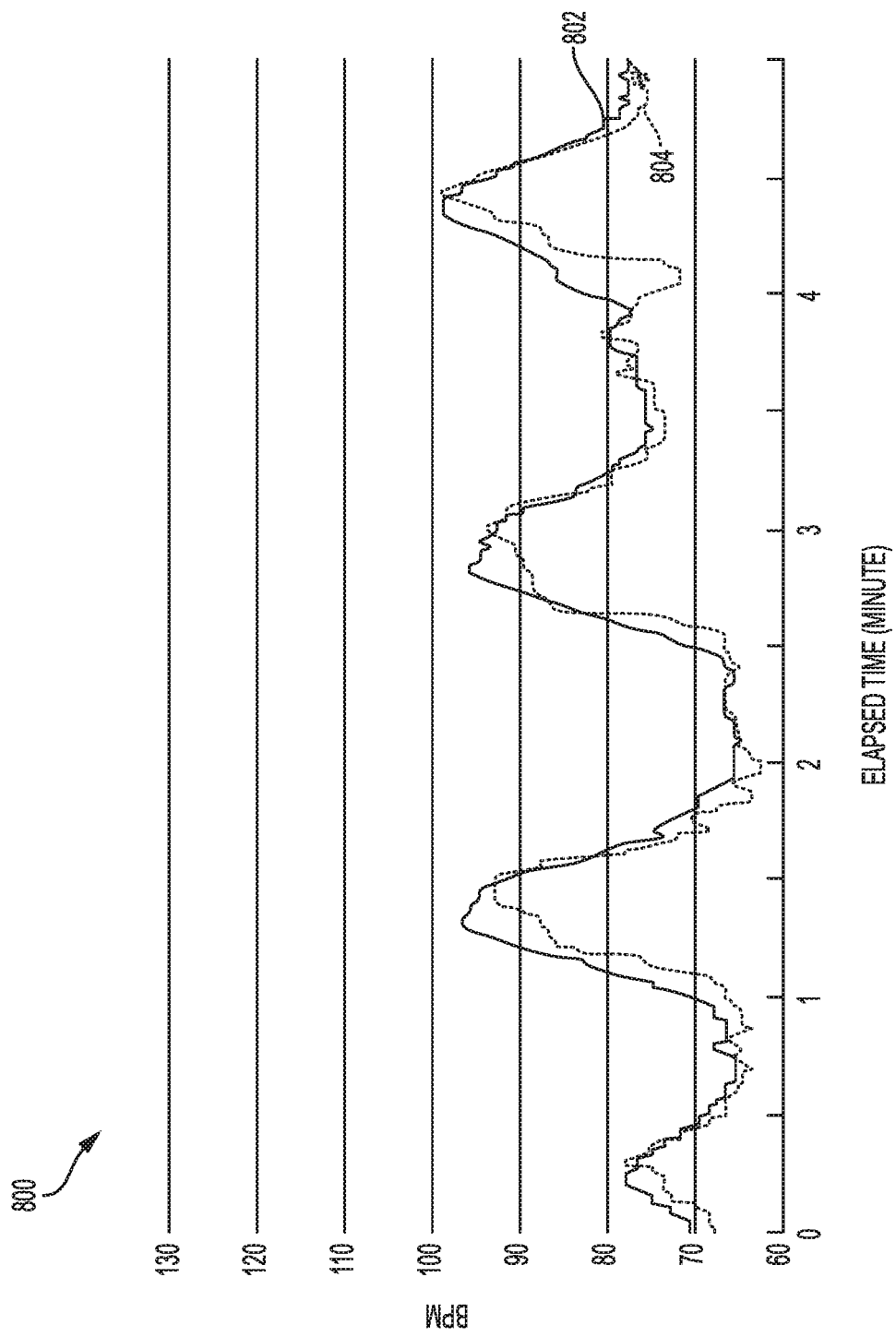
Figure 9:
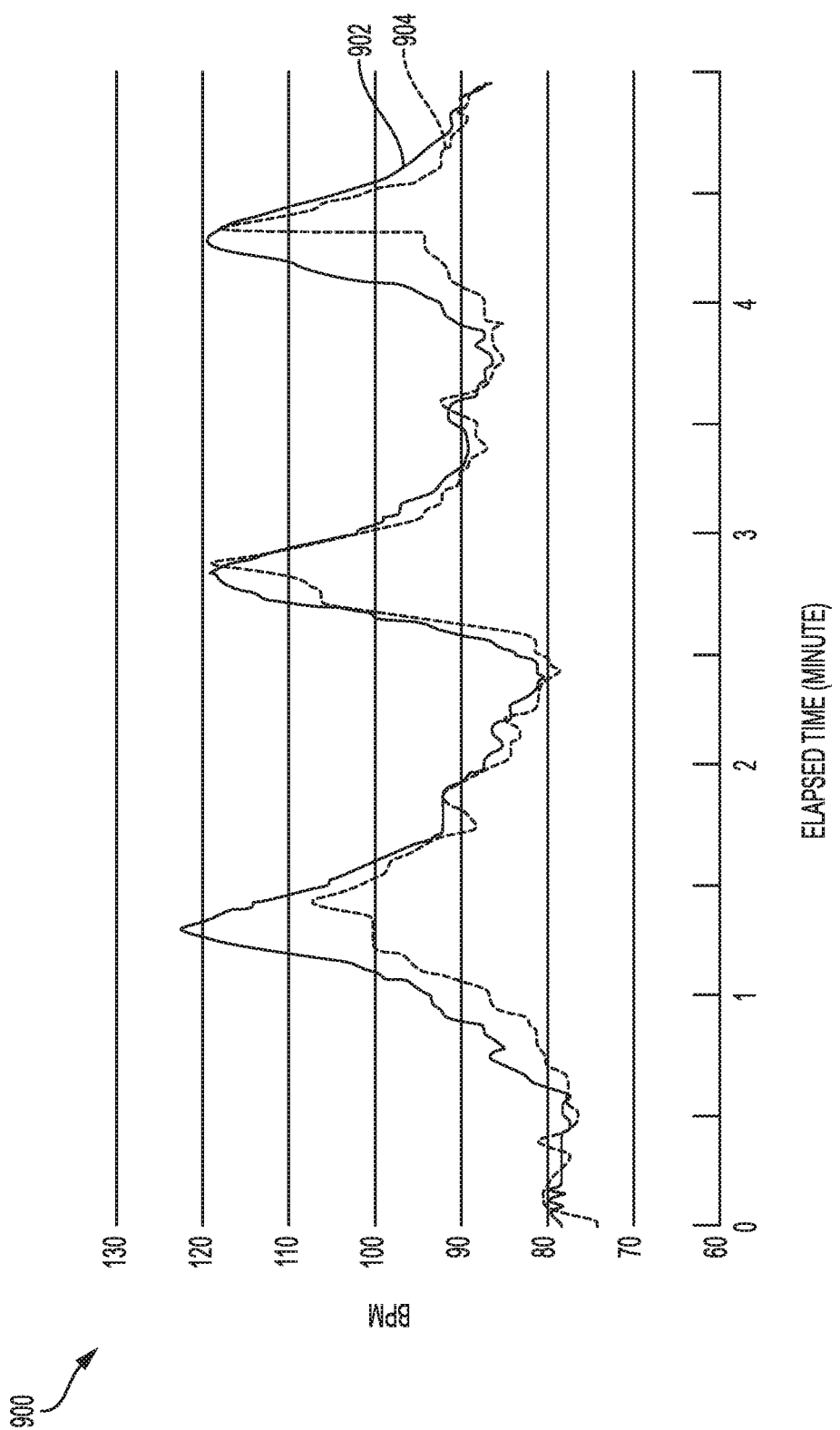
Figure 10:
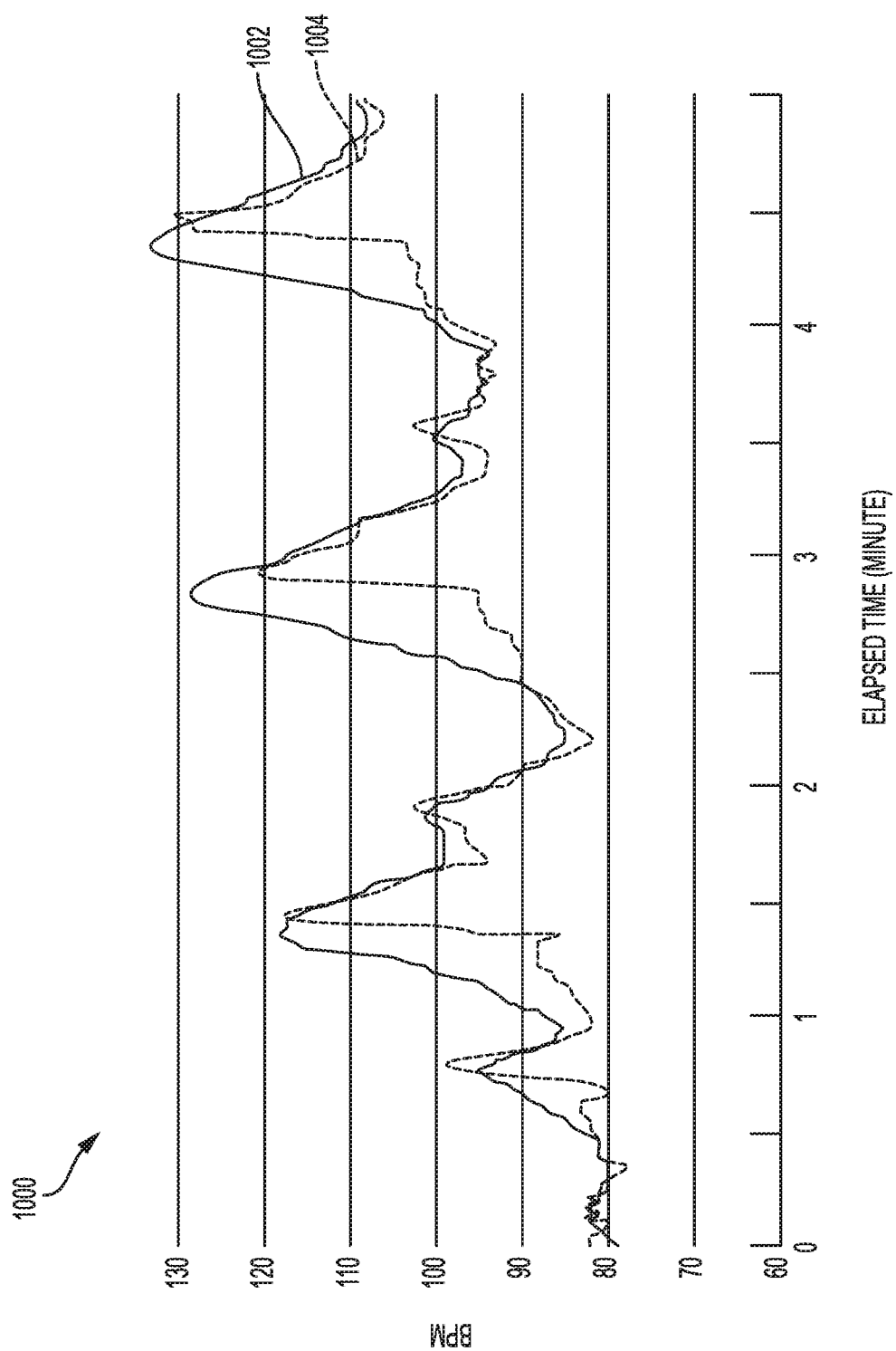

FIG. 6 illustrates a method 600 for determining and utilizing an intensity level according to some embodiments of the present disclosure. In some embodiments, method 600 can determine the intensity level of an exercise which a person performs based on the person's heart rate measured by a PPG sensor. In some embodiments, method 600 can be modified by, for example, having blocks combined, divided, rearranged, changed, added, and/or removed.

At block 602, a body movement(s) is detected. For example, one or more sensors (e.g., gyroscope 250 and accelerometer 260 in motion sensor 240 (FIG. 2)) can detect a person's body movements.

At block 604, the detected body movements can be analyzed. In some embodiments, the body movement information can be used to determine whether the person has started to exercise. In some embodiments, the body movement information can be used to determine the type of exercise that the person is performing. For example, the person can perform a barbell bench press while wearing wearable device 100 (FIG. 1). Based on the body movement information, wearable device 100 or another device (e.g., companion device 300 (FIG. 3)) can determine that the person is performing or has performed a barbell bench press.

In some embodiments, the body movement information can be used to determine the skill level or experience level of the person for the exercise that the person is performing. For example, if the person is a novice in weight training and performs a barbell bench press, the person is likely to be wobbly when pushing and pulling the weight. Motion sensor 240 can detect that the person is being wobbly, and wearable device 100 or another device (e.g., companion device 300) can determine that the person is a novice in weight training and/or in the barbell bench press exercise. As another example, if the person is more experienced or advanced, the person is likely to be stable in performing a barbell bench press. In this case, motion sensor 240 can detect the stability in performing the barbell bench press, and wearable device 100 or another device can determine that the person is experienced or advanced in weight training and/or in the barbell bench press exercise. In some embodiments, the level of the person's skills or experience can be determined based on the amount of the stability that motion sensor 240 detects. In some embodiments, the rate at which the user performs the two phases of the exercise can determine how familiar the user is with the exercise. For example, if the ratio of concentric to eccentric contraction is less than 1:2, then the user is likely a novice. As another example, if the ratio is 1:2, it can be determined that the intensity is likely less and/or the user is warming up. In some embodiments, motion sensor 240 may need to be calibrated. For example, motion sensor 240 can be calibrated by the person lifting a dumbbell as directed. In some embodiments, the person can manually enter information related to when the exercise has started or ended, and/or information related to the person's experience level.

At block 606, the person's heart rate can be determined using a PPG sensor. For example, the person can wear wearable device 100 with heart rate sensor 290 (FIG. 2) using PPG to determine the person's heart rate. In some embodiments, the person's heart rate can be determined periodically.

At block 608, the determined heart rate can be analyzed. In some embodiments, a PPG graph can be drawn, where the person's heart rate is plotted against the time period. In some embodiments, the PPG graph can be compared with other graphs or data in a library of experimental data (e.g., as described in block 412 (FIG. 4)). For example, the library can be searched to determine whether there is a graph whose shape is the same or similar to the shape of the PPG graph. In some embodiments, this search can involve analyzing the signatures of the graphs in the library and comparing them with the signature of the PPG graph. As another example, a lag in detecting a change in the heart rate by the PPG sensor can be analyzed. For example, in the experimental data shown in FIGS. 7-10, 14-17, 21-24, and 28-31, there is generally a lag in detecting an increase in the heart rate by the PPG sensor compared to the ECG sensor. The amount of this lag can be dependent on various factors, including the exercise type and the intensity level. In some embodiments, the shape of the PPG curve can determine the type of exercise performed. In some embodiments, the heart rate recovery, which can be the time to baseline after the exercise is completed, can be indicative of the overall fitness level of the user. In some embodiments, the determined heart rate can be analyzed in the same way as described in the present disclosure without using any graphs. For example, when the determined heart rate is compared with other data (e.g., data in the library of experimental data), analytical techniques, such as numerical analysis and statistical analysis, can be used. In some embodiments, a person's heart rate can be determined periodically over a period of time before the analysis is performed on a set of the determined heart rates. For example, a person's heart rate can be determined every second for a five-minute period. In this example, there would be 300 determined heart rates that can be analyzed together. The length of this period can be set manually or automatically. In some embodiments, the length can be automatically set such that the analysis can provide optimal results.

At block 610, an intensity level can be determined based at least on the analysis of the heart rate. In some embodiments, the intensity level of the exercise can be determined based on the intensity level associated with the matching graph found in the library of experimental data. For example, a person can perform a bench press and the person's heart rate measured by the PPG sensor may show a curve whose shape is similar to a portion of lighter curve 704 in FIG. 7. A system or device can recognize this similarity and determine that the person is performing the bench press at 40% intensity. As another example, the lag shown in the PPG-measured heart rate from block 606 can be determined to be similar to the lag shown in lighter curve 704 in FIG. 7. A system or device can recognize this similarity and determine that the person is performing the bench press at 40% intensity. In some embodiments, the intensity level determination can take other factors into account. These other factors can include the person's age, gender, weight, height, skill level for the given exercise, experience level for the given exercise, medical history, and current physical condition. In some embodiments, the intensity level determination can also take the following factors into account: the determined skill level and/or the determined experience level from block 604. In some embodiments, statistical analysis can be performed to determine a confidence level for the determined intensity level. For example, during the initial stage of an exercise, the confidence level can be low because the amount of PPG-measured heart rate data is small. In some embodiments, other measures in addition to, or in place of the intensity level can be determined. For example, a level of efforts can be determined.

At block 612, coaching information can be provided. This coaching information can help a person with an exercise program by, for example, providing a training methodology that can be more efficient and/or effective. For example, if a person wants to build strength and the person is not training at an optimal intensity level, the person can be provided with information on whether the intensity level should be increased or decreased. In some embodiments, the coaching information can be produced based at least on the determined intensity level. For example, if the optimal intensity level for an exercise for a person is 90% but the person is currently performing the exercise at 30%, the person can be coached to increase the intensity level to 90%.

In some embodiments, the person can be coached by sound and/or visual display that is provided by a device(s), such as wearable device 100 (FIG. 1) and companion device 300 (FIG. 3). The coaching information can also be provided based on one or more of other factors, such as the person's age, gender, experience level, activity level, medical condition, medical history, training history, or training goals. For example, a person can be in a specific training program that lasts between eight and twenty-six weeks. During various points in the training period, specific intensity levels may be desired to meet the training goals. The person can be provided with coaching information that fits the training program. In some embodiments, coaching information can be used to support a rehabilitation program. In some embodiments, methods for providing coaching information can be implemented as an application that can be installed and executed on one or more devices, such as wearable device 100 and companion device 300.

Experiments have been performed on various exercise types to test the relationship between the PPG-measured heart rate and the intensity level. The data gathered from these experiments can be used in implementing a system or method of using the PPG-measured heart rate as an intensity indicator. Twelve people participated in these experiments. Three of them were novices (i.e. they had not performed weight training before), three of them were at an intermediate level (i.e. they had performed weight training for a short period of time), and the remaining three were at an advanced level (i.e. they had performed weight training for a long period of time). The experiments involved performing four different types of exercises—bench press, military press, lat pulldowns, and dumbbell curls—at eleven different intensities while wearing a chest strap device with an ECG sensor and also wearing a wrist strap device with a PPG sensor on the left wrist. For each exercise type at each intensity, each person performed a five-minute test, where three sets of eight reps at the specific intensity were performed over a five-minute period. The first set was performed at minute 1, the second set was performed at minute 2.5, and the third set was performed at minute 4. The person performed the specific exercise for each intensity for the five-minute period from the lowest intensity level to the highest intensity level, with five-minute breaks in between tests. Heart rates were measured at one-second intervals. The reference devices (heart rate sensor) reported heart rate at an interval of 1 second. Initial data collected from these experiments on one person is described below in connection with FIGS. 7-34. These figures show four of the eleven intensities for illustrative purposes.

FIGS. 7, 8, 9, 10, 14, 15, 16, 17, 21, 22, 23, 24, 28, 29, 30, and 31 show graphs 700, 800, 900, 1000, 1400, 1500, 1600, 1700, 2100, 2200, 2300, 2400, 2800, 2900, 3000, and 3100, respectively. In each of these graphs, the darker curve (702, 802, 902, 1002, 1402, 1502, 1602, 1702, 2102, 2202, 2302, 2402, 2802, 2902, 3002, and 3102) represents the heart rate measured using the chest strap device with the ECG sensor. The lighter curve (704, 804, 904, 1004, 1404, 1504, 1604, 1704, 2104, 2204, 2304, 2404, 2804, 2904, 3004, and 3104) represents the heart rate measured using the wrist strap device with the PPG sensor. The ECG-measured heart rate provides the reference heart rate, to which the PPG-measured heart rate is compared. Thus, in each of these figures, the difference between the two curves can show the error in the PPG-measured heart rate.

Figure 11:
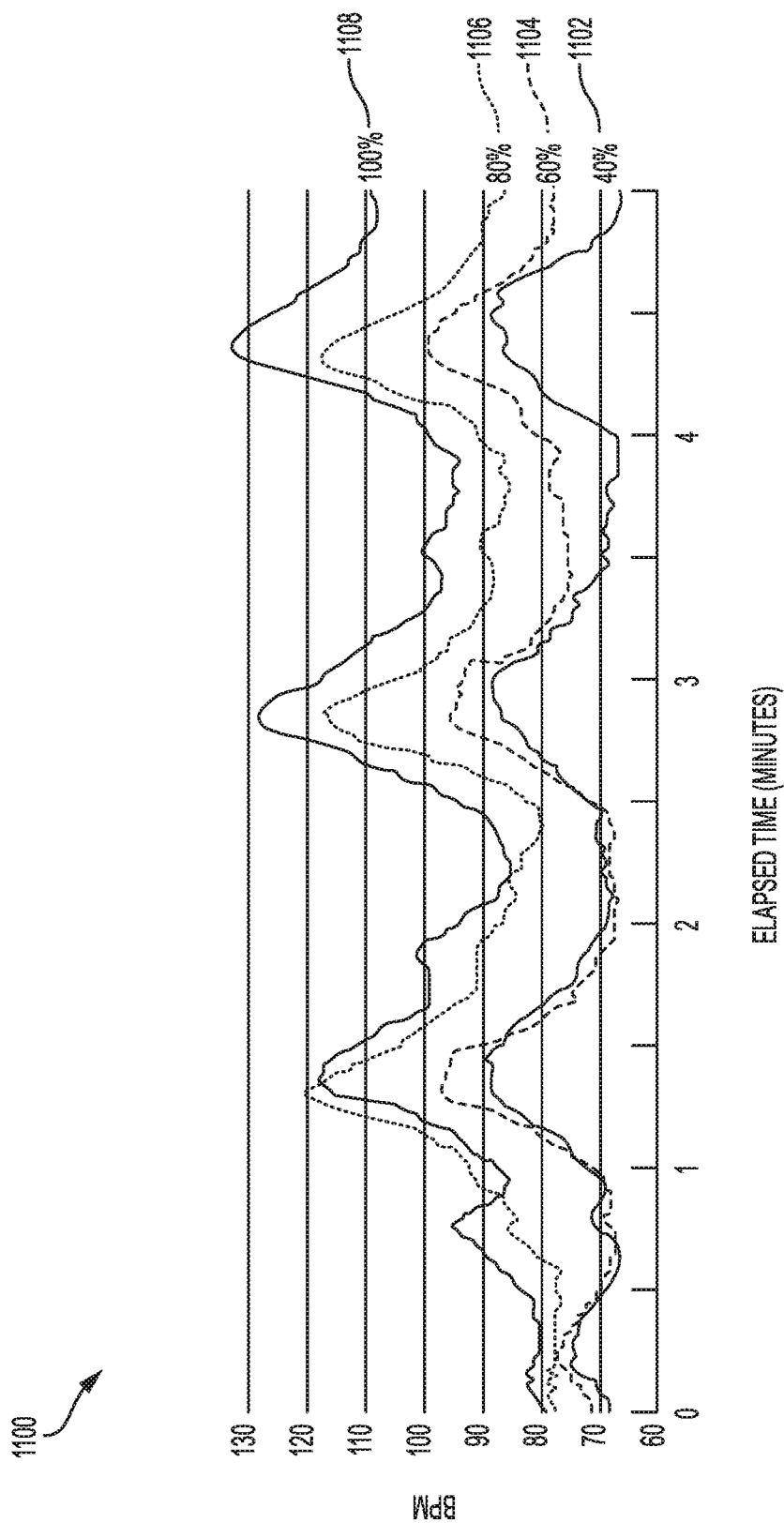
Figure 12:
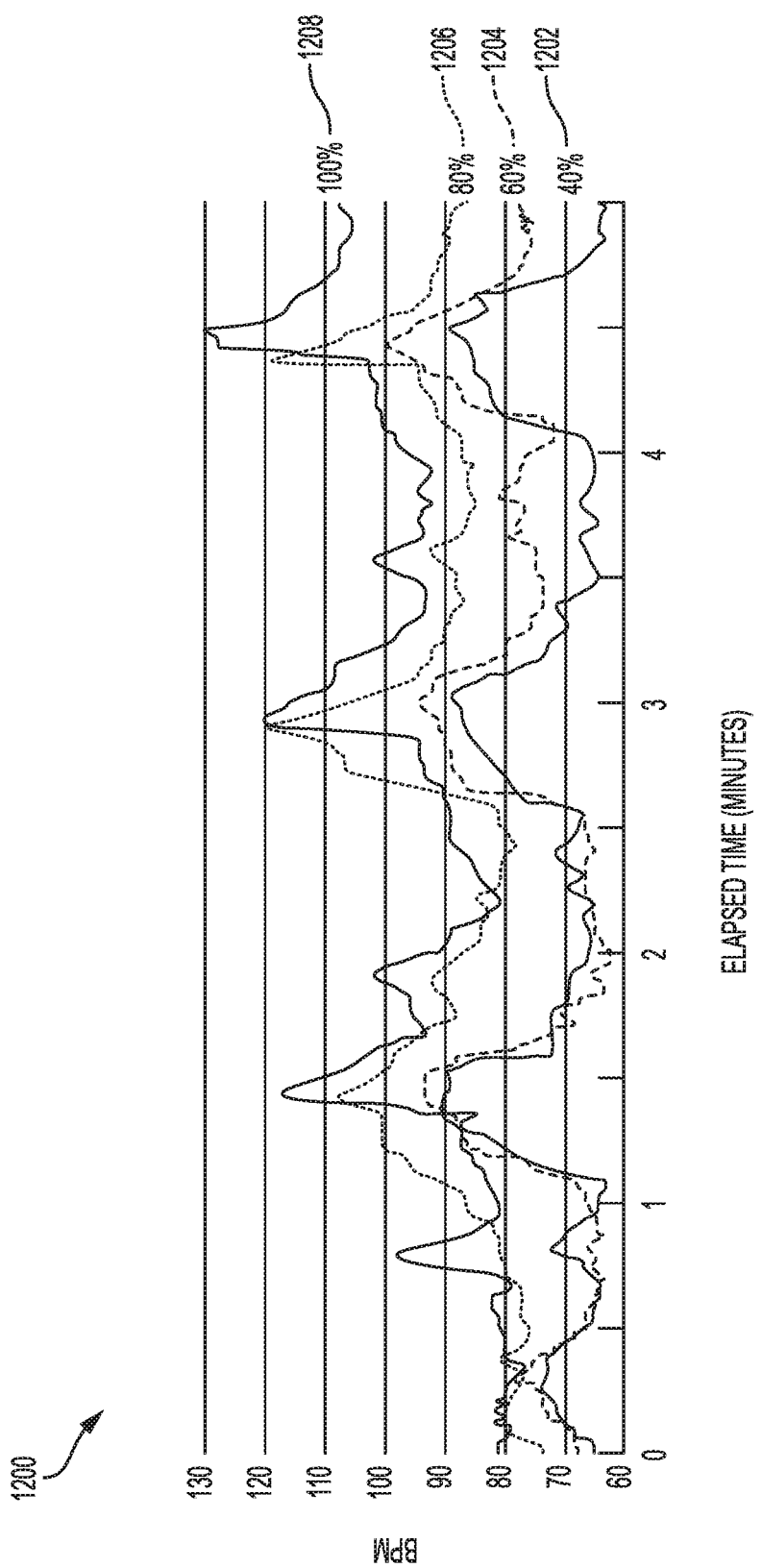
Figure 13:
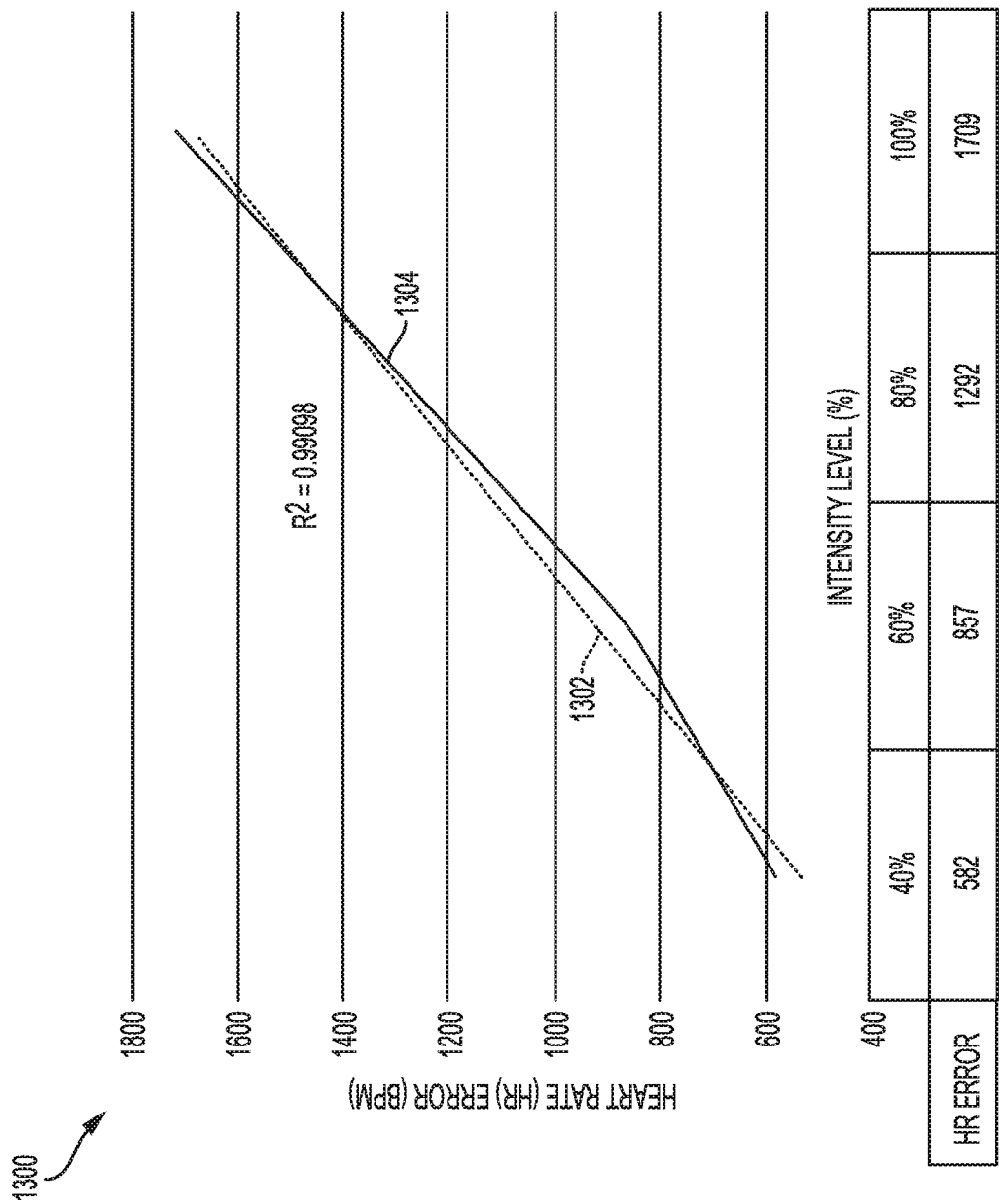
Figure 14:
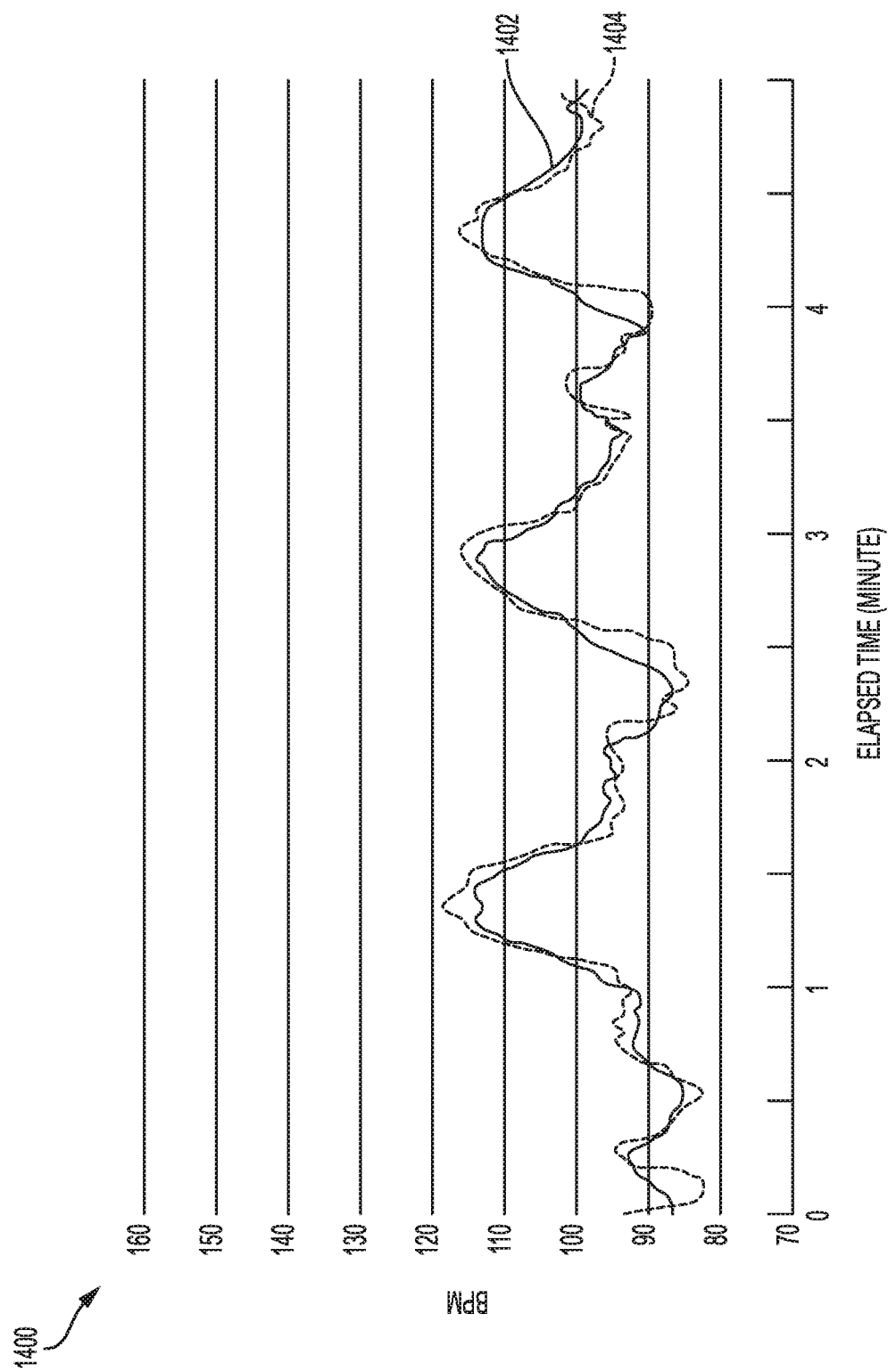
FIGS. 14-20 show graphs drawn using experimental data associated with performing a military press exercise.
Figure 15:
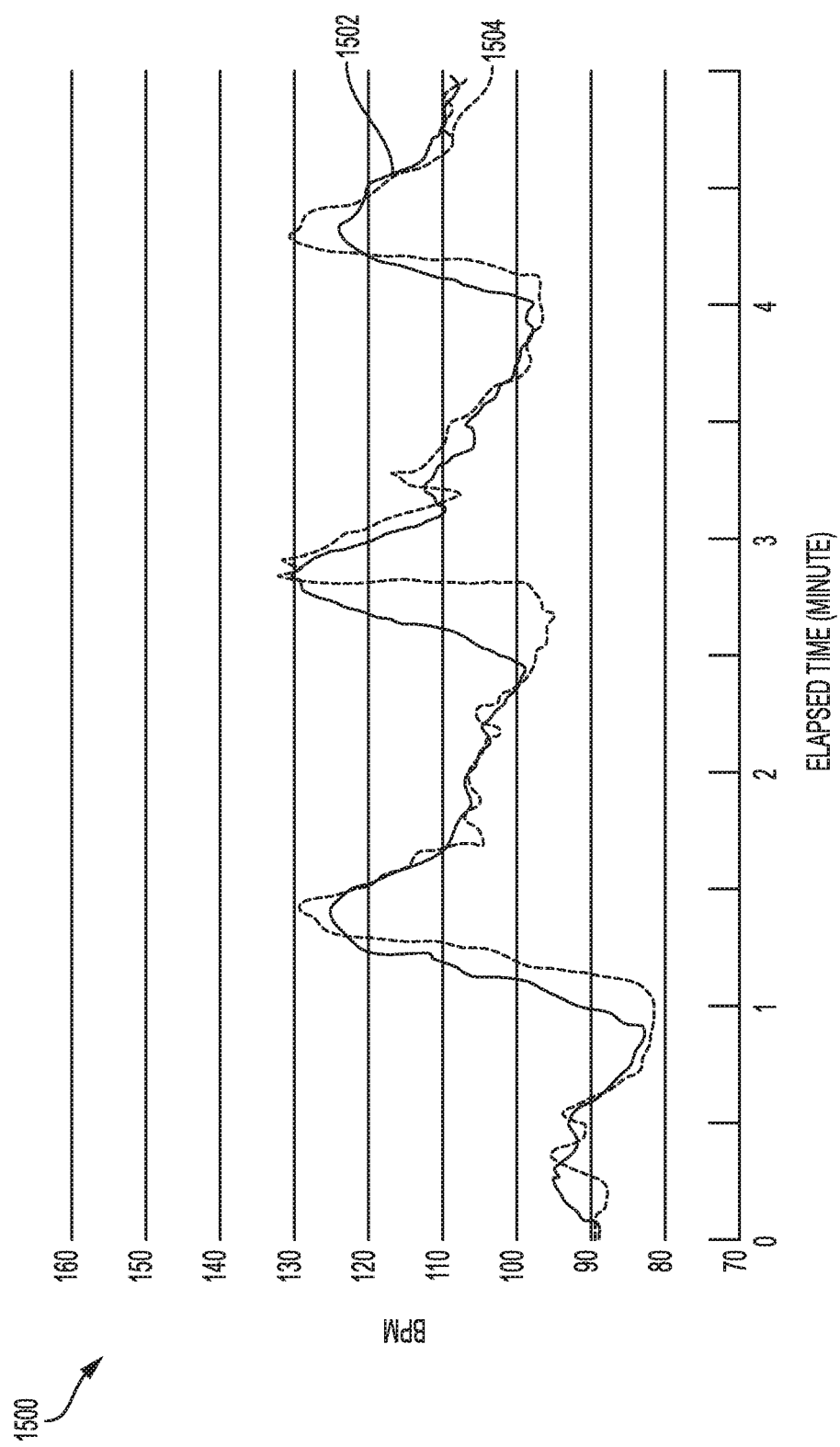
Figure 16:
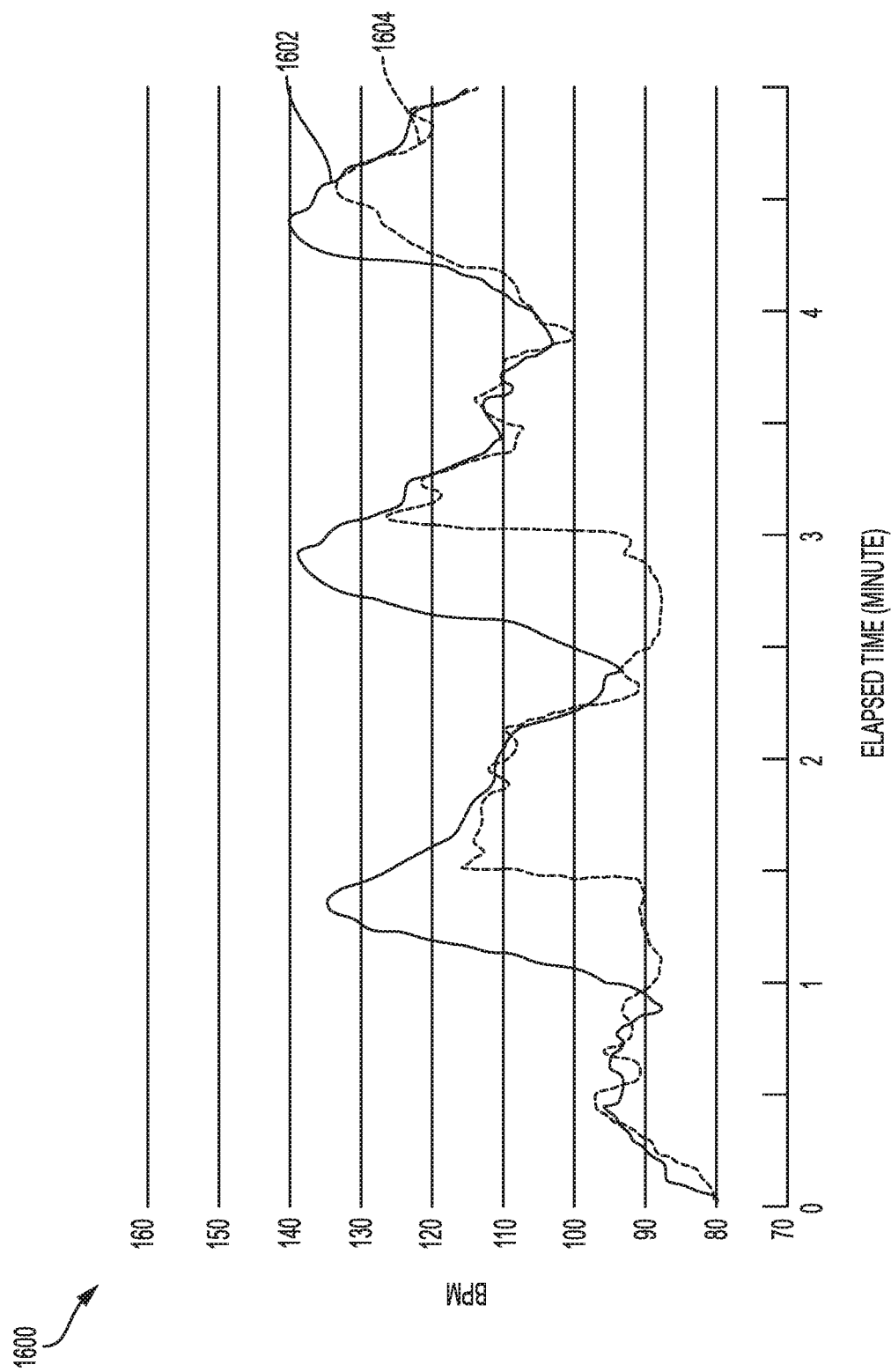
Figure 17:
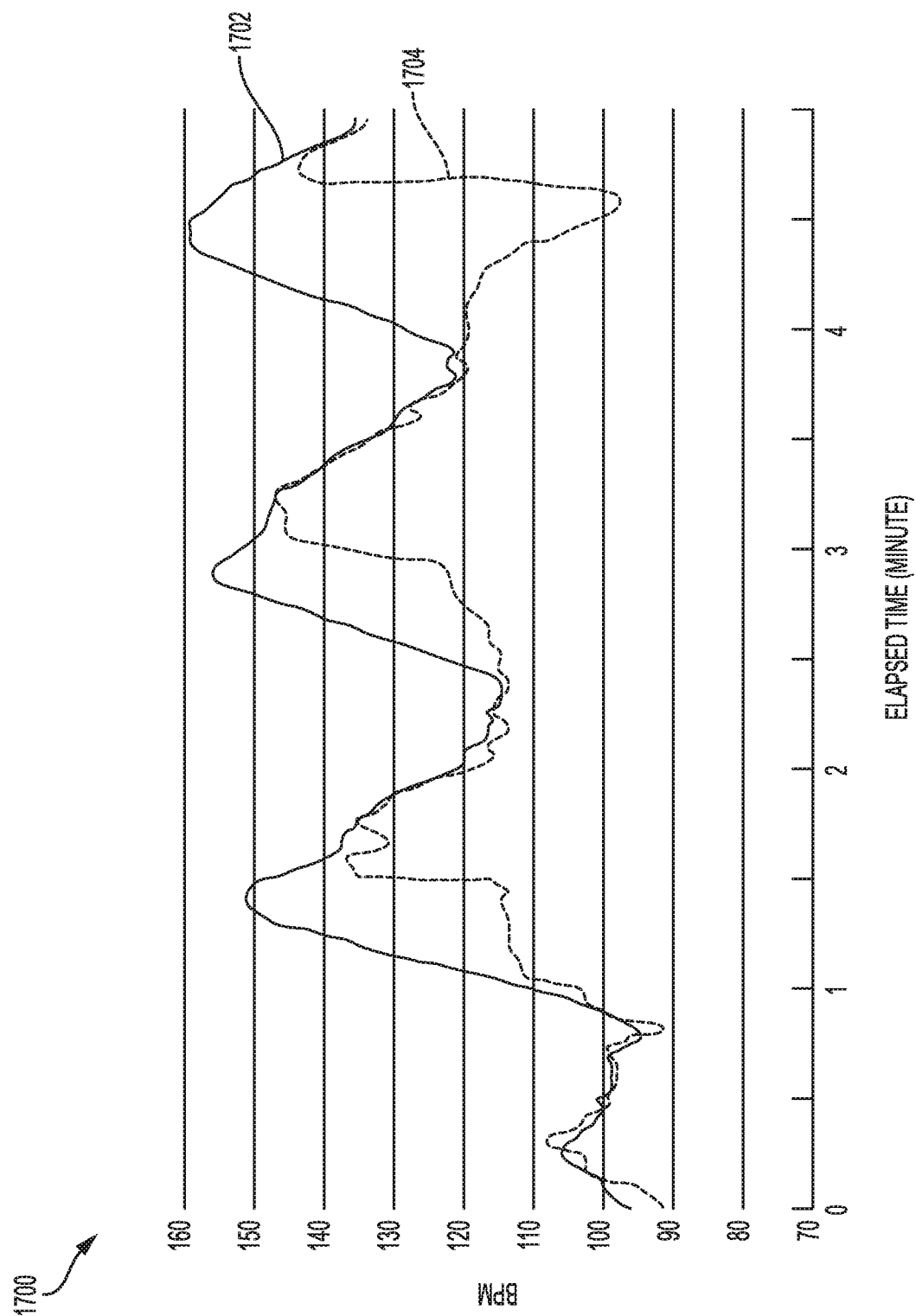

FIGS. 7, 8, 9, and 10 show experimental data from both the chest strap and wrist strap devices for bench press performed with 74 lbs, 111 lbs, 148 lbs, and 185 lbs of weights, respectively. These weights respectively represent the intensity levels of 40%, 60%, 80%, and 100%. The absolute value error sums in FIGS. 7, 8, 9, and 10 are 582 beats per minute (BPM), 857 BPM, 1292 BPM, and 1709 BPM, respectively. FIG. 11 shows a graph 1100 illustrating experimental data from the chest strap device for bench press performed at 40% (1102), 60% (1104), 80% (1106), and 100% (1108) intensity. FIG. 12 shows a graph 1200 illustrating experimental data from the wrist strap device for bench press performed at 40% (1202), 60% (1204), 80% (1206), and 100% (1208) intensity. FIG. 13 shows a graph 1300 with a regression curve 1302 (dotted line) and a curve 1304 (solid line) that is created by plotting the error in the PPG-measured heart rate against the intensity level. The R-squared value is 0.99098.

Figure 18:
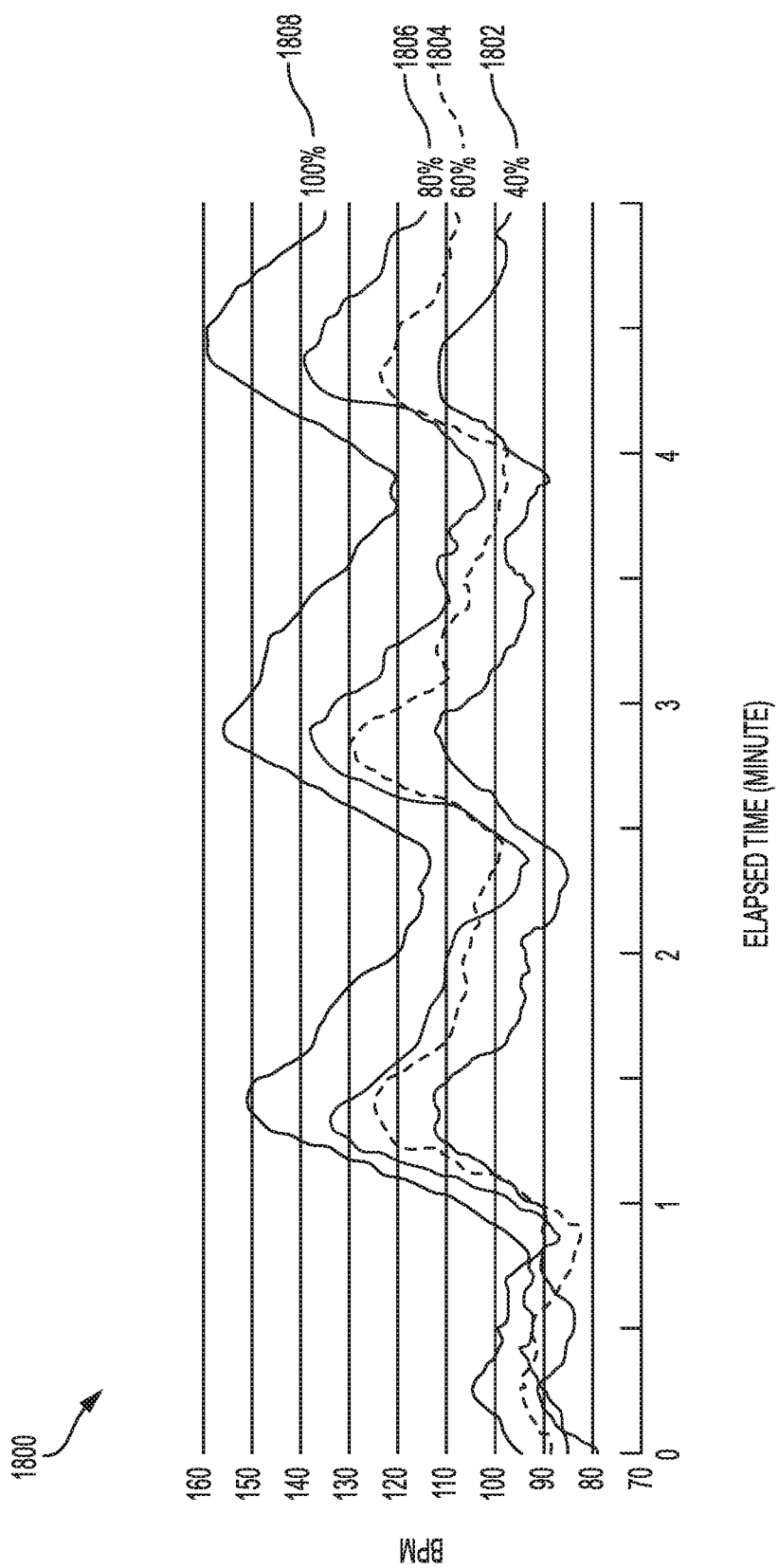
Figure 19:
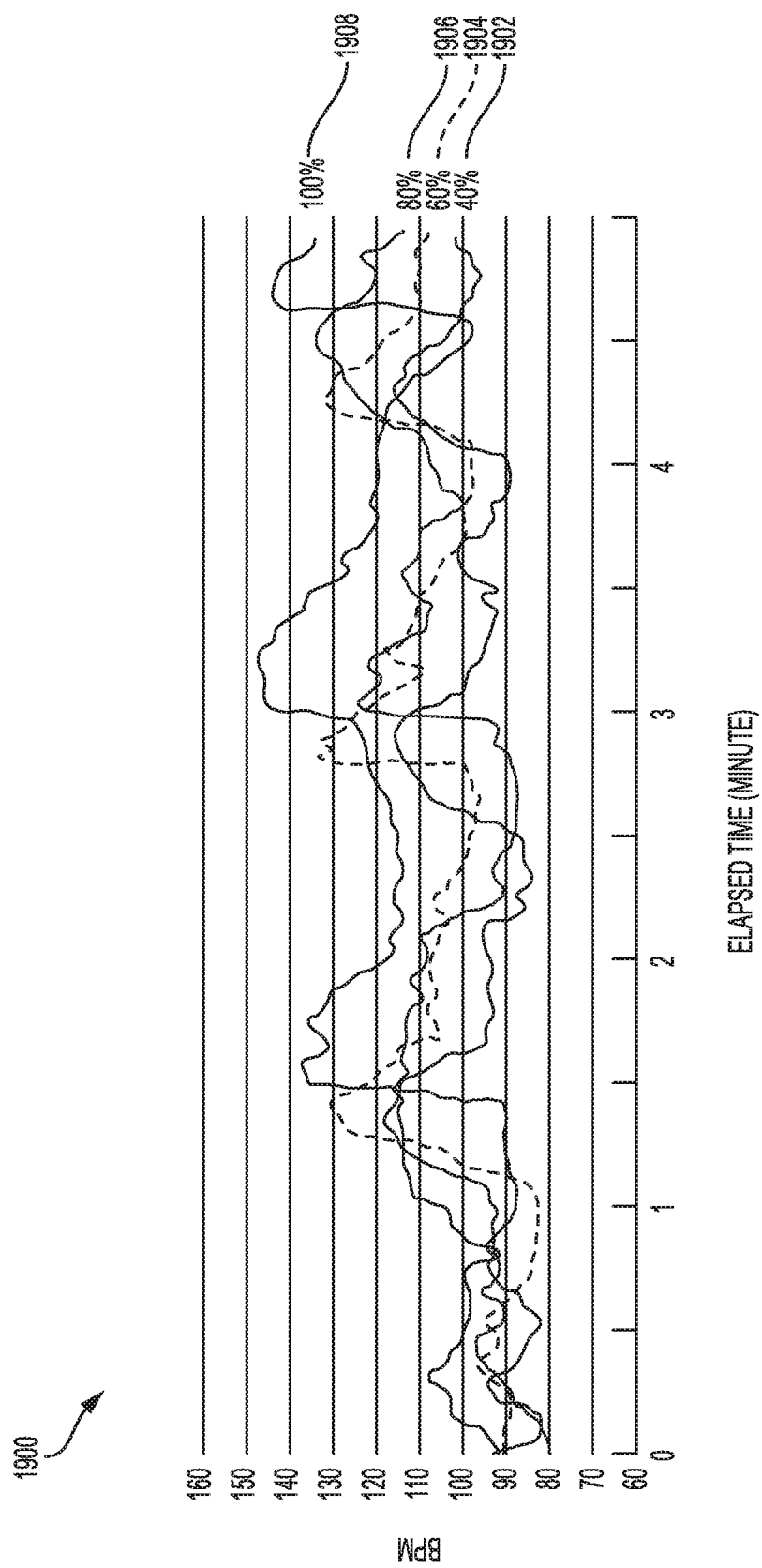
Figure 20:
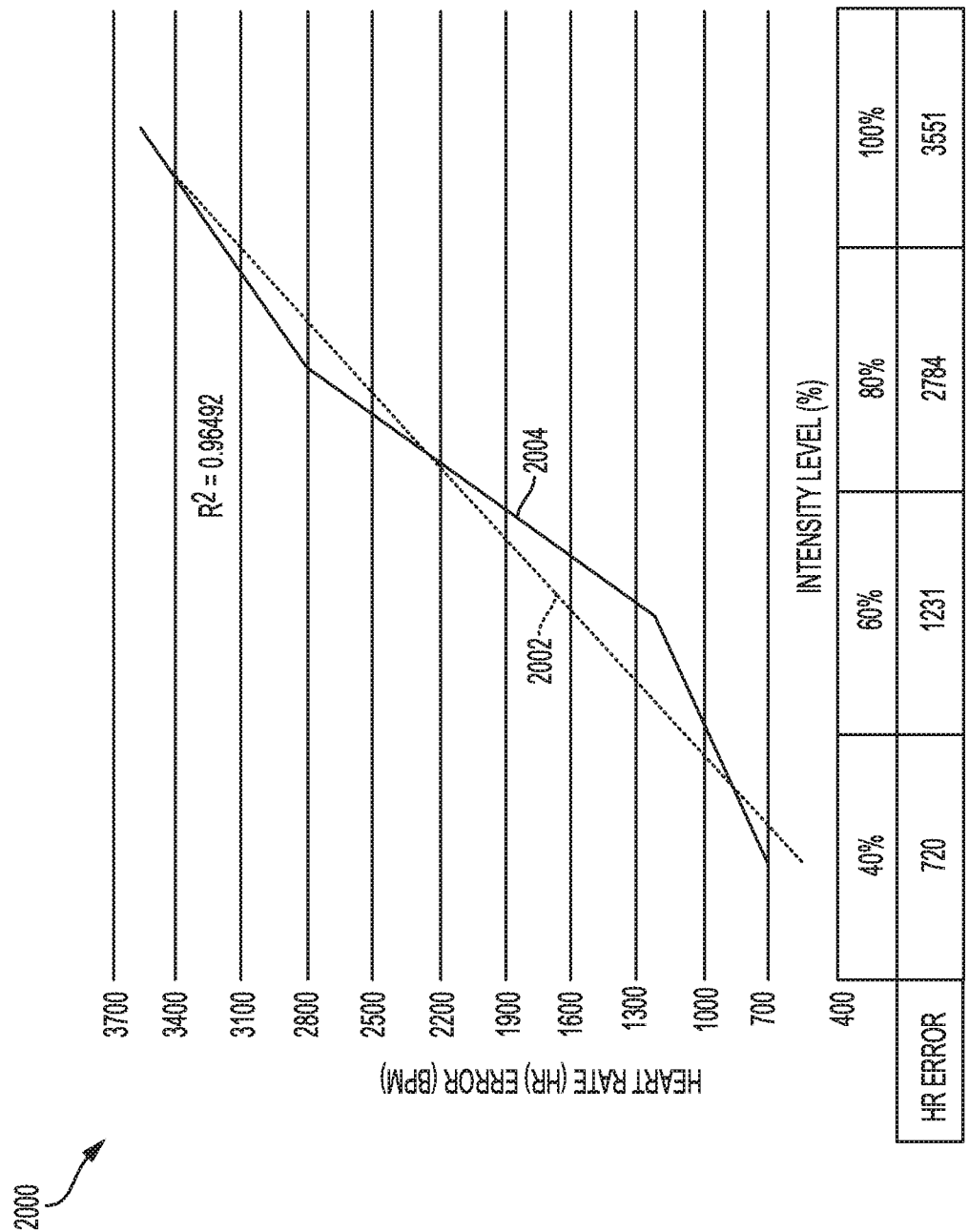
Figure 21:
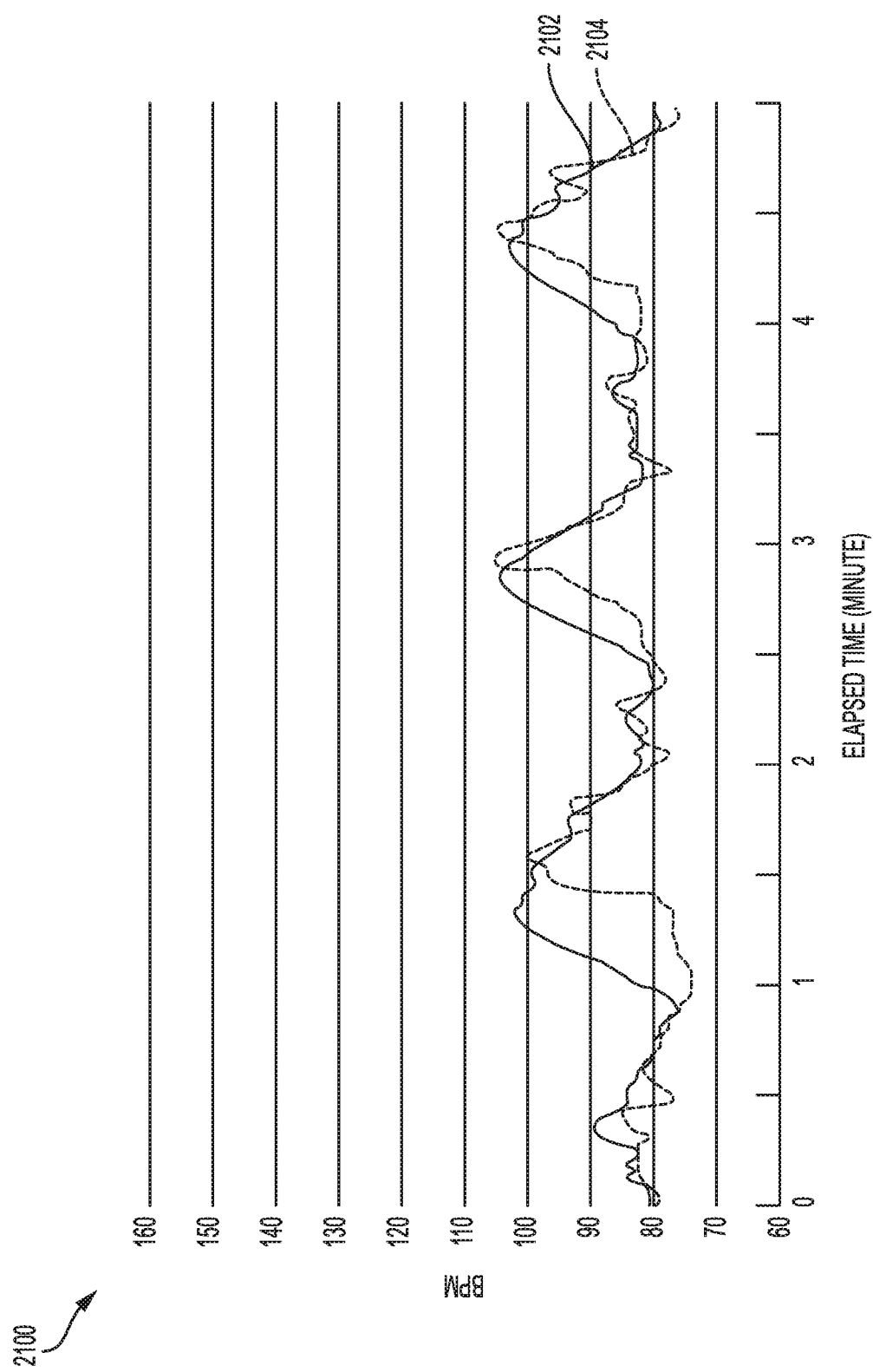
FIGS. 21-27 show graphs drawn using experimental data associated with performing a lat pulldowns exercise.
Figure 22:
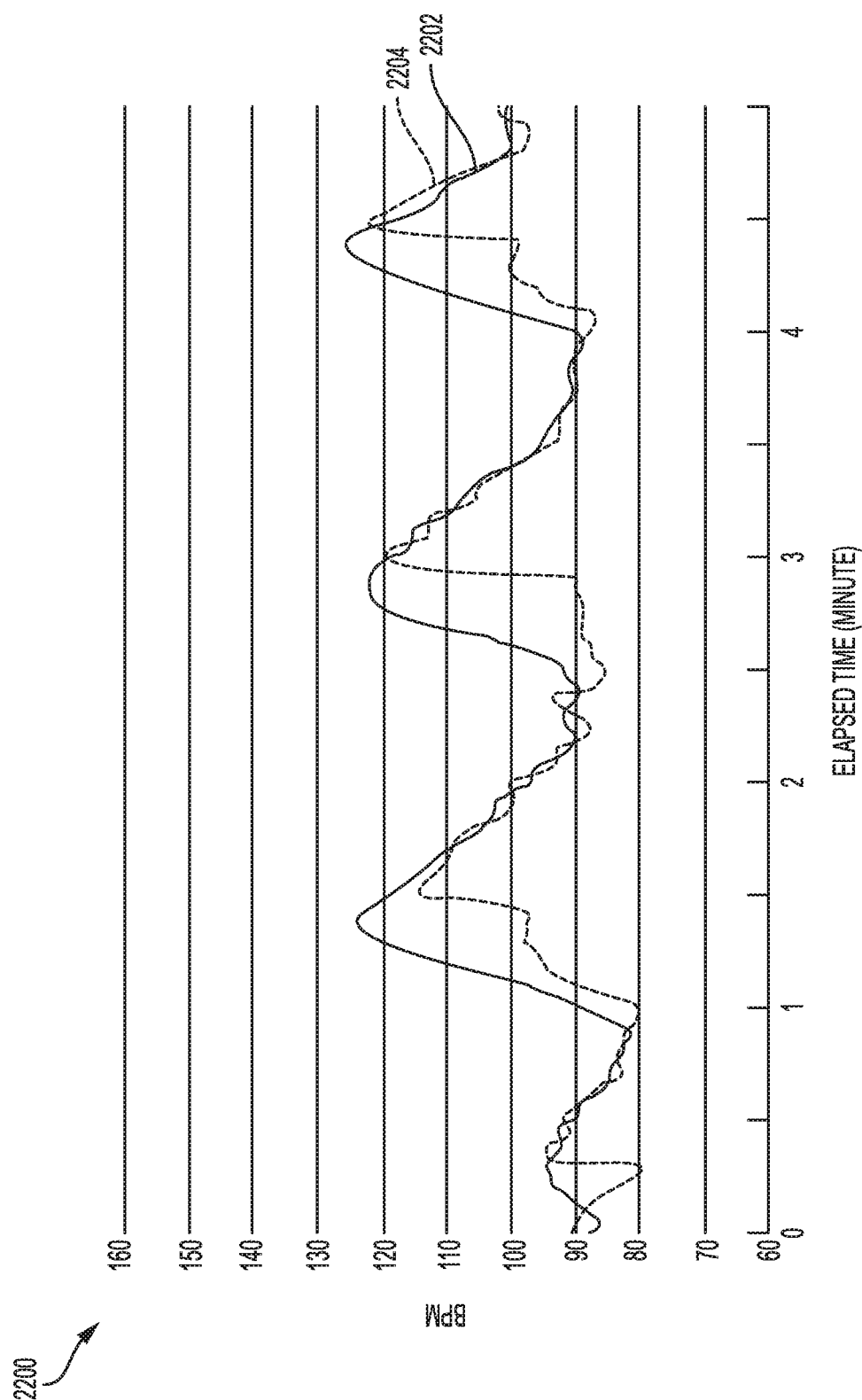
Figure 23:
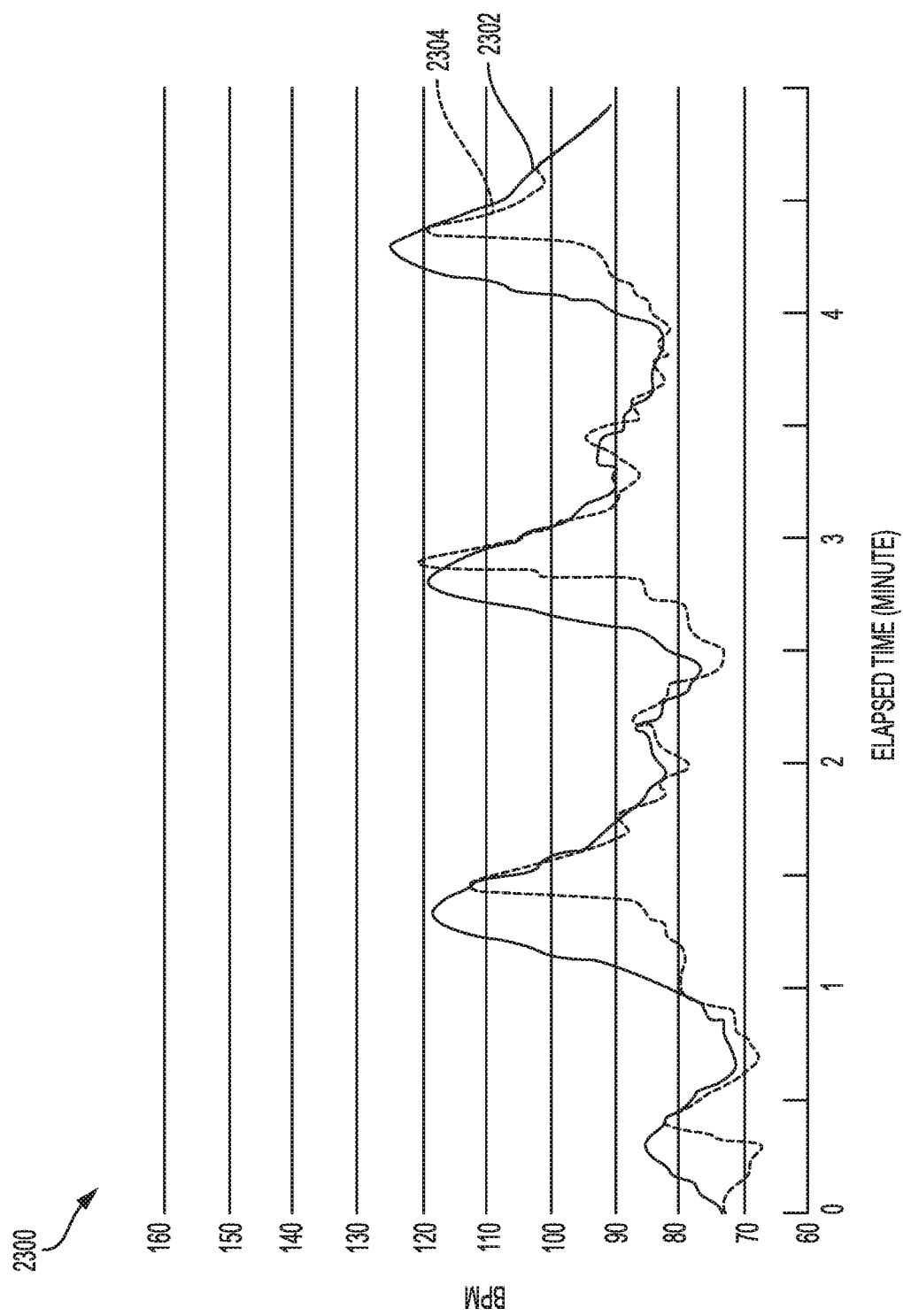
Figure 24:
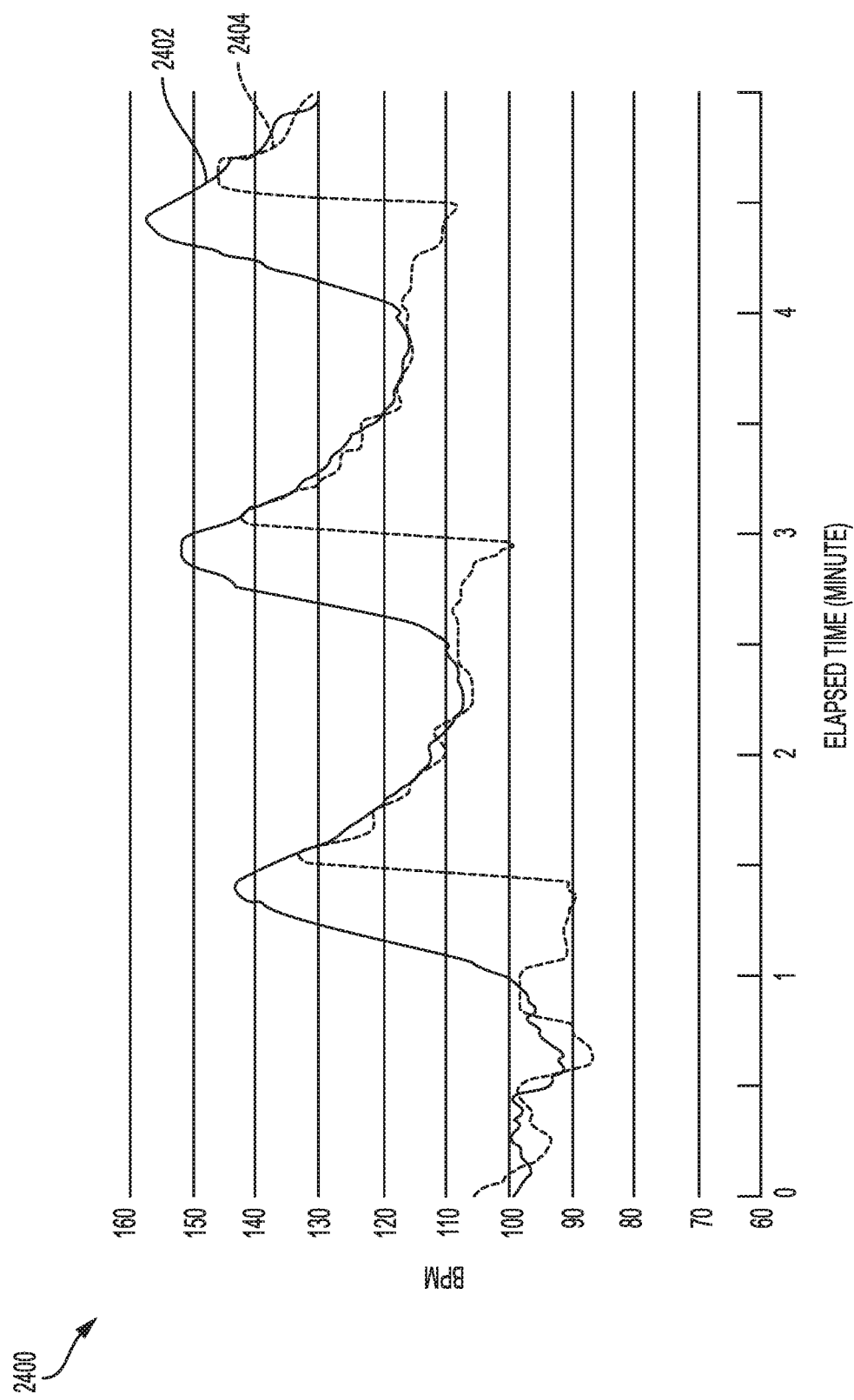

FIGS. 14, 15, 16, and 17 show experimental data from both the chest strap and wrist strap devices for military press performed with 24 lbs, 36 lbs, 48 lbs, and 60 lbs of weights, respectively. These weights respectively represent the intensity levels of 40%, 60%, 80%, and 100%. The absolute value error sums in FIGS. 14, 15, 16, and 17 are 720 BPM, 1231 BPM, 2784 BPM, and 3551 BPM, respectively. FIG. 18 shows a graph 1800 illustrating experimental data from the chest strap device for military press performed at 40% (1802), 60% (1804), 80% (1806), and 100% (1808) intensity. FIG. 19 shows a graph 1900 illustrating experimental data from the wrist strap device for military press performed at 40% (1902), 60% (1904), 80% (1906), and 100% (1908) intensity. FIG. 20 shows a graph 2000 with a regression curve 2002 (dotted line) and a curve 2004 (solid line) that is created by plotting the error in the PPG-measured heart rate against the intensity level. The R-squared value is 0.96492.

Figure 25:
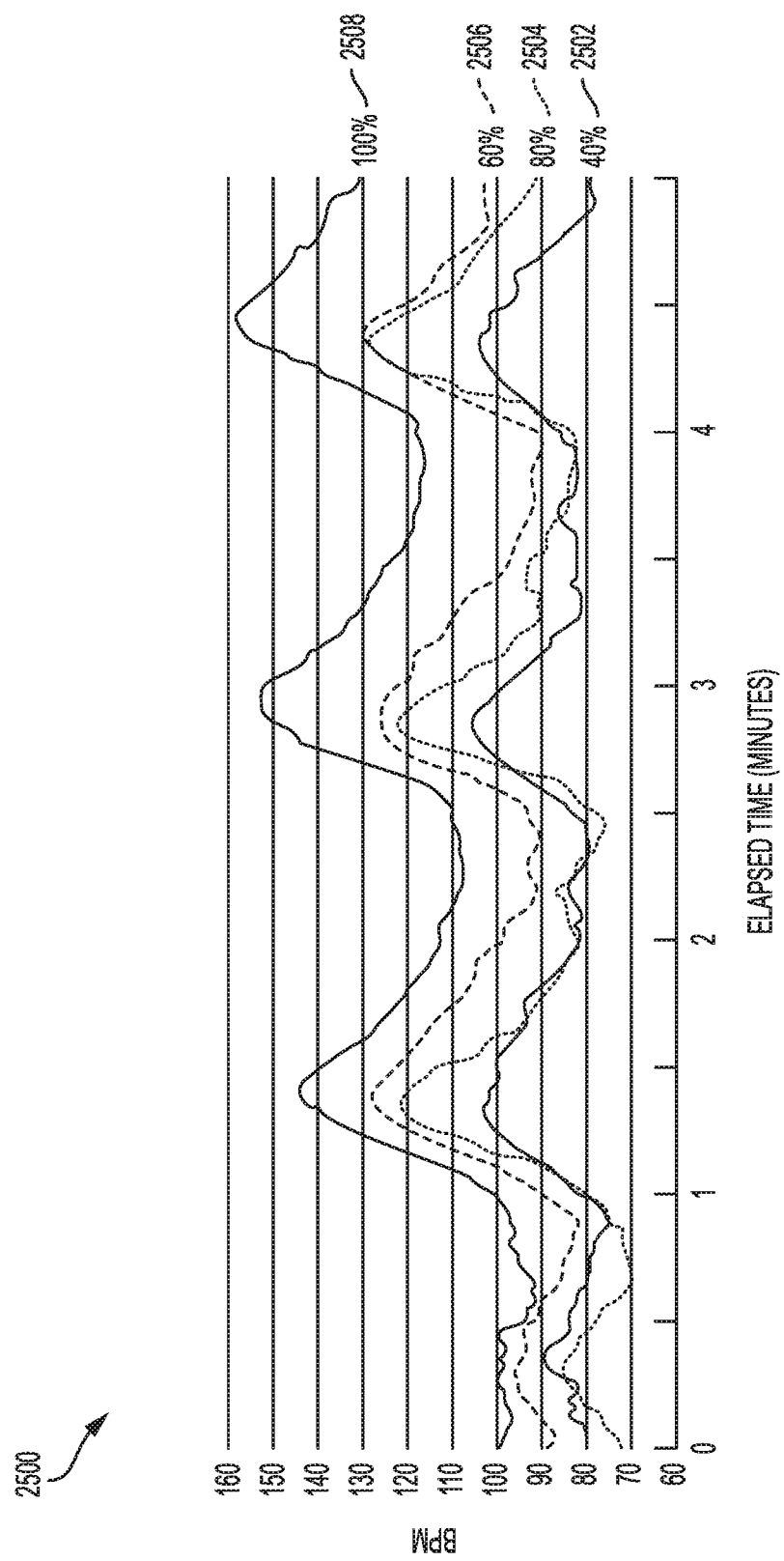
Figure 26:
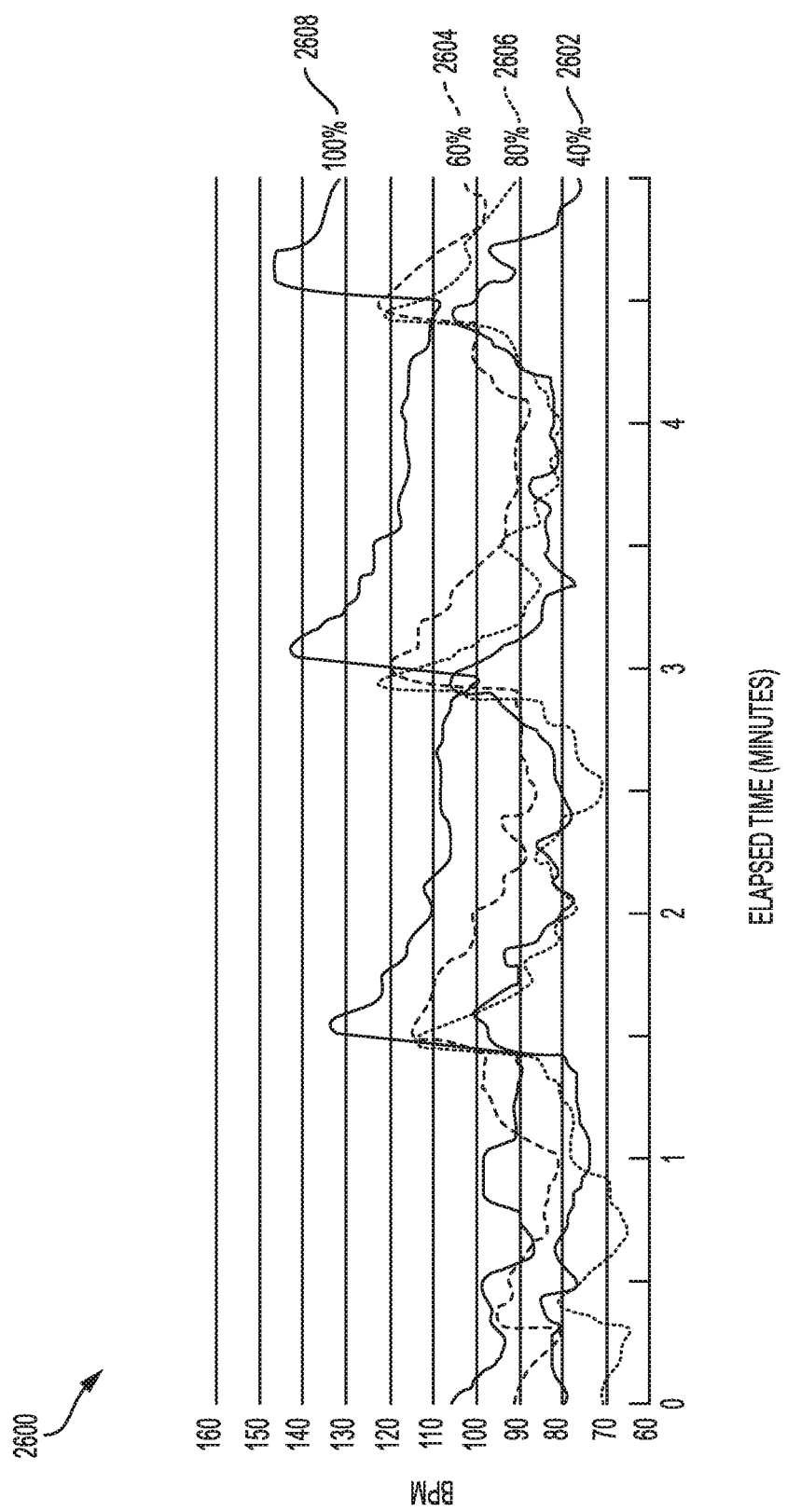
Figure 27:
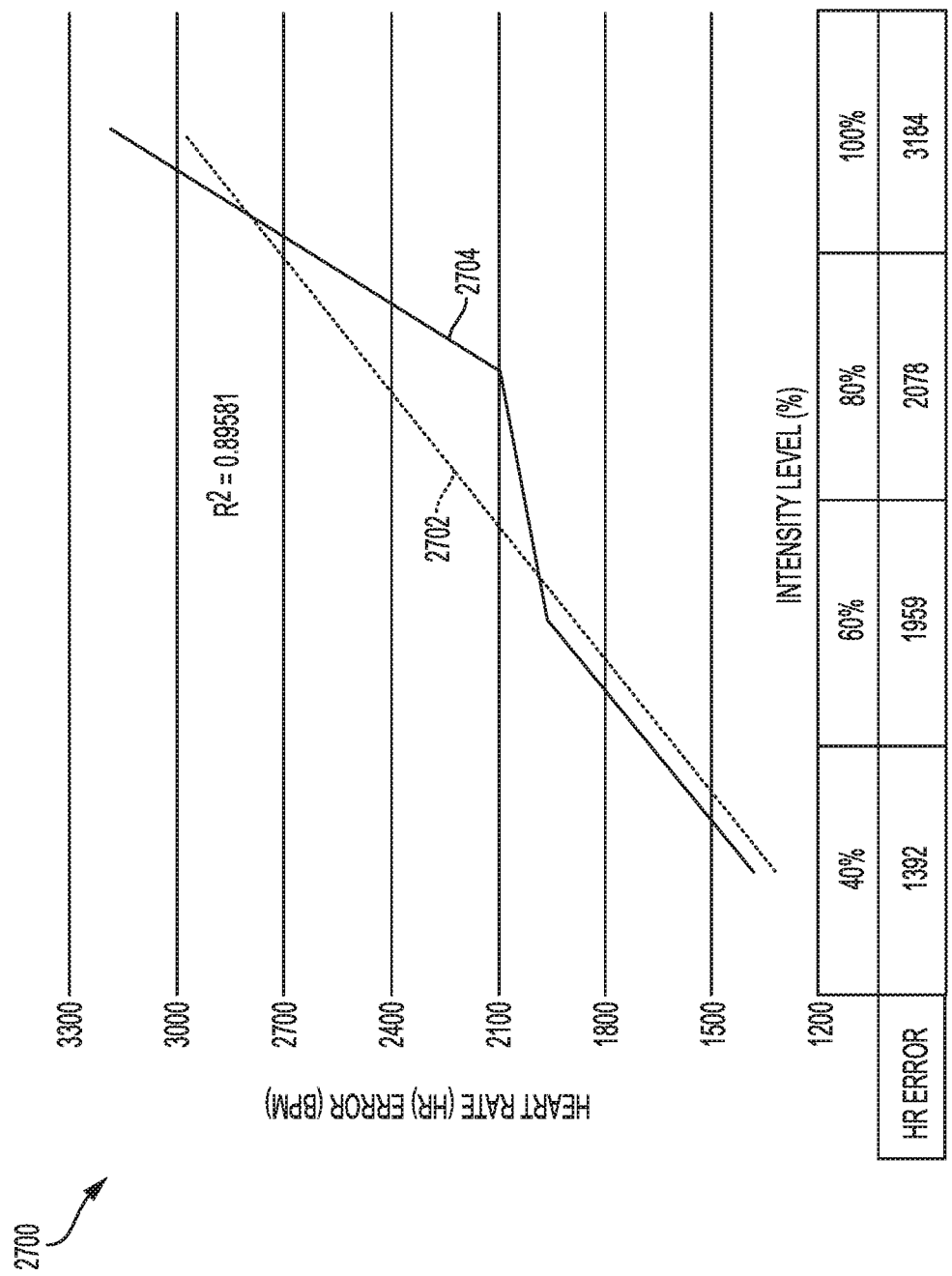
Figure 28:
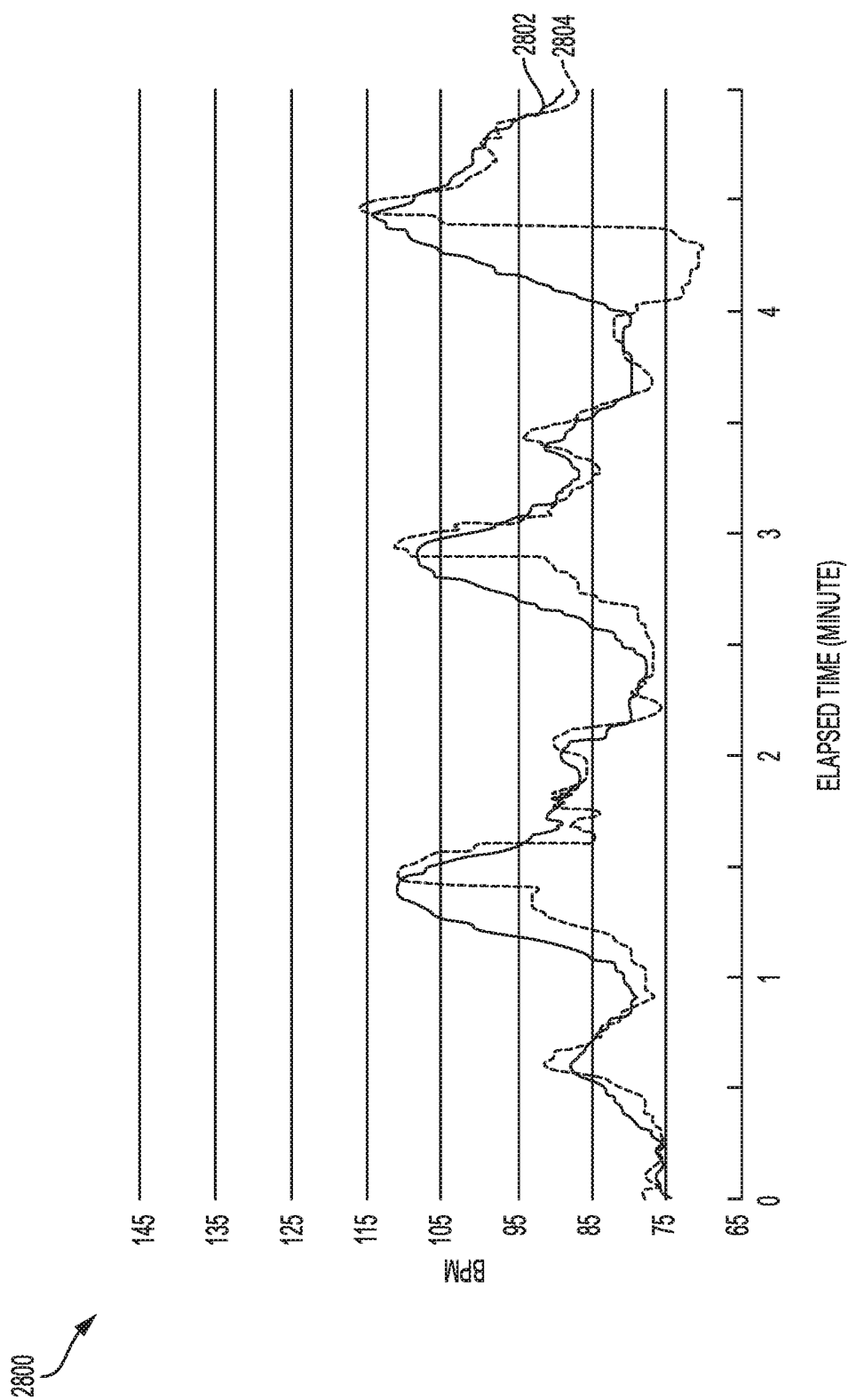
FIGS. 28-34 show graphs drawn using experimental data associated with performing a dumbbell curls exercise.
Figure 29:
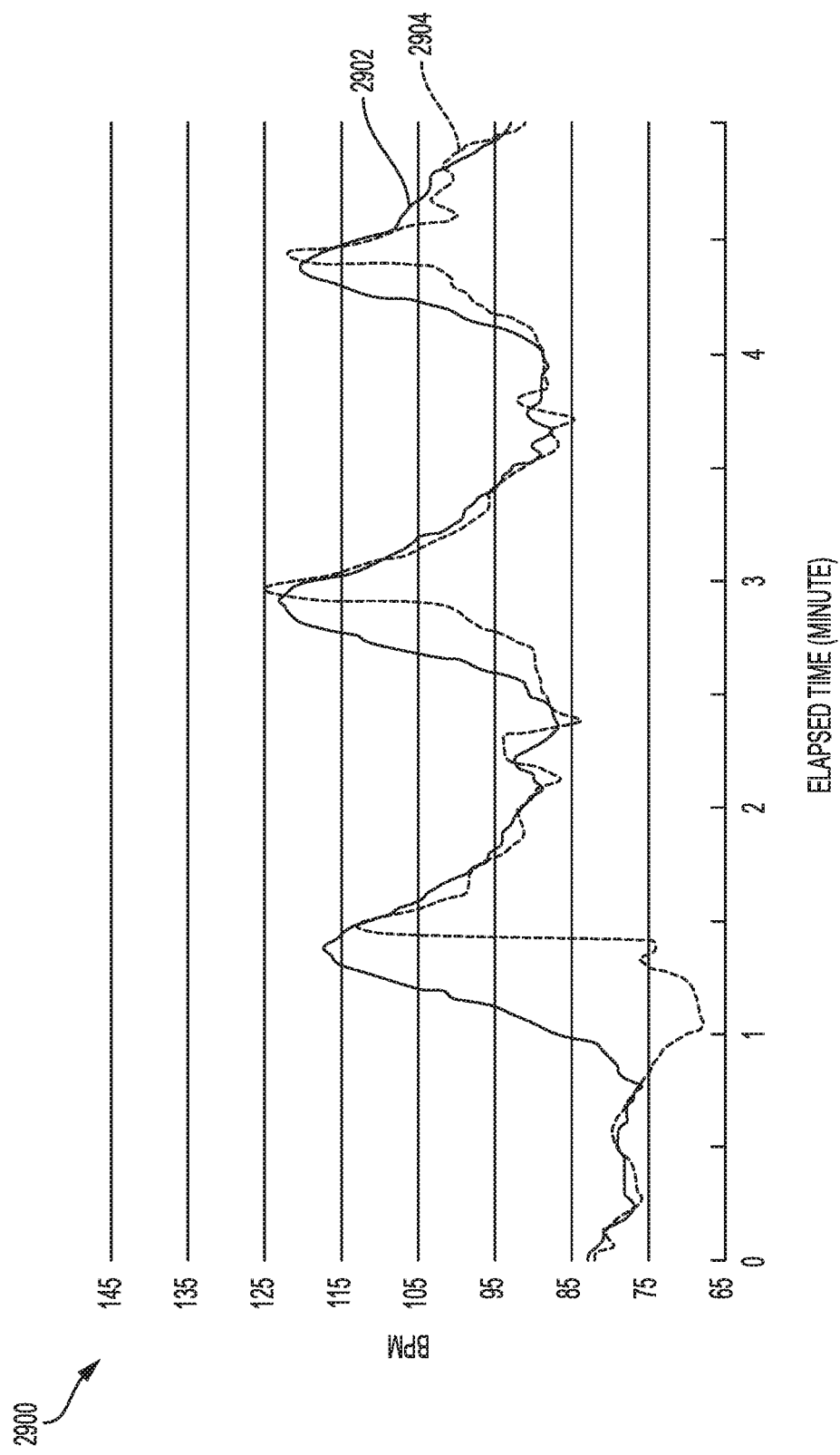
Figure 30:
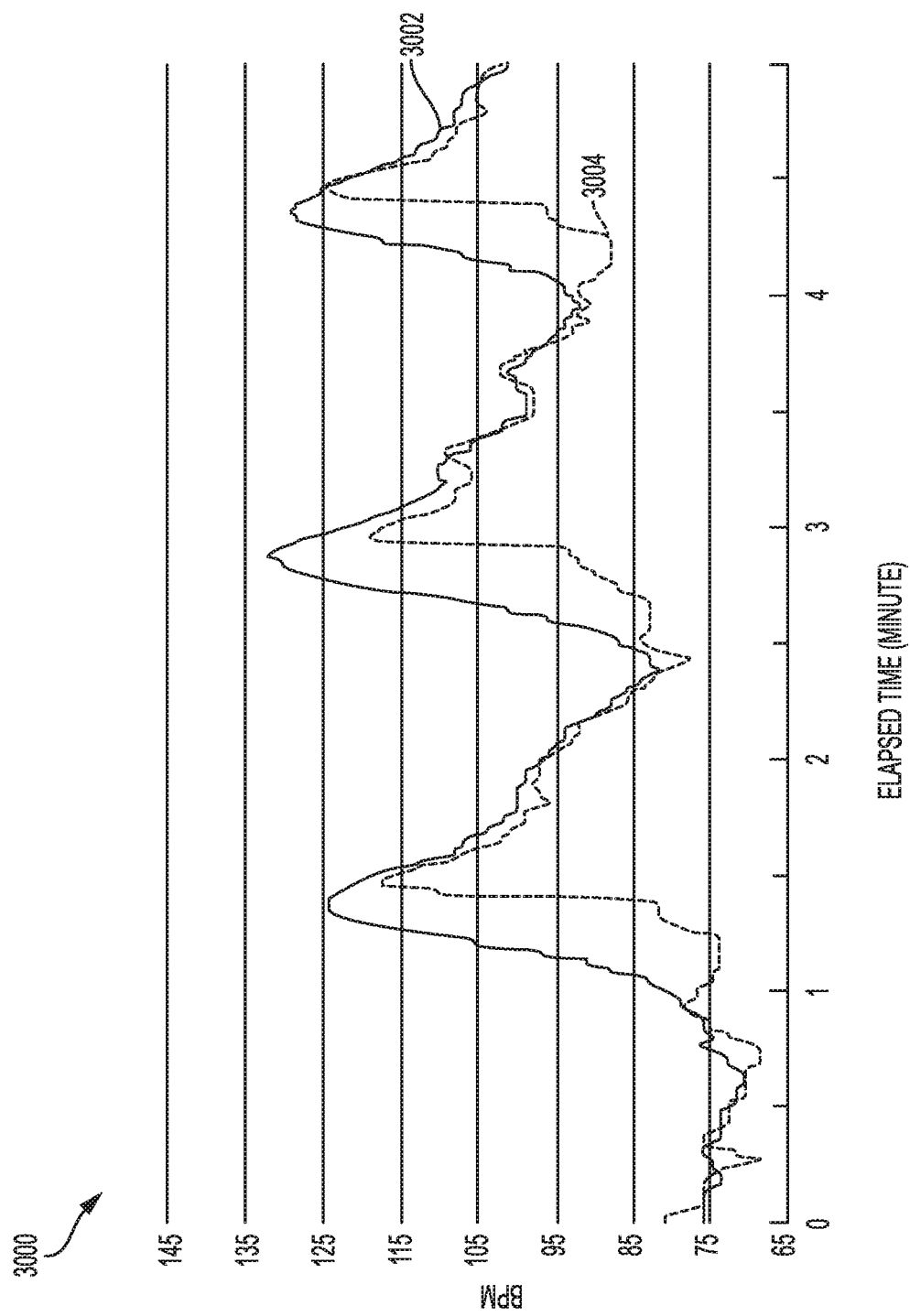
Figure 31:
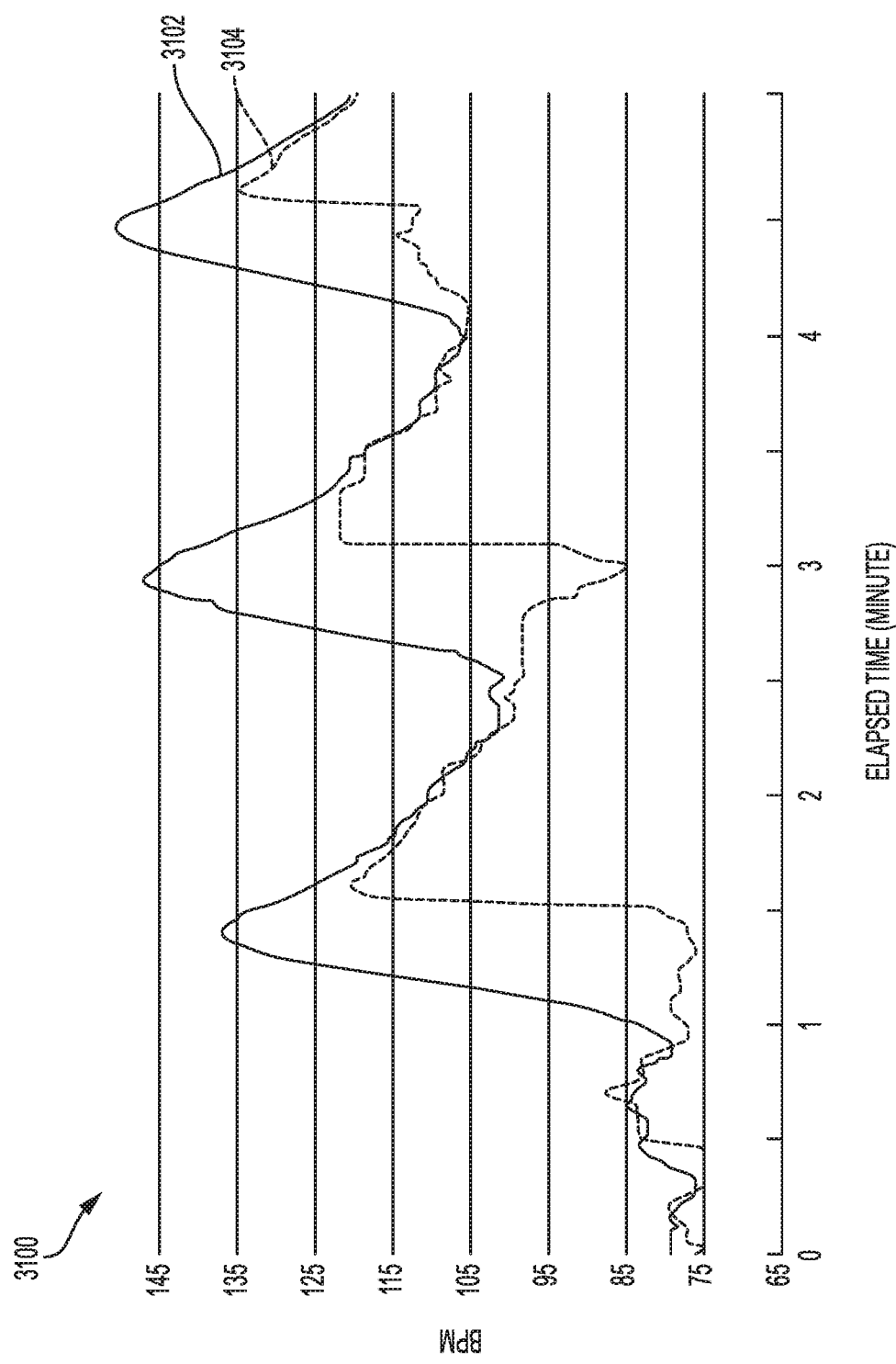

FIGS. 21, 22, 23, and 24 show experimental data from both the chest strap and wrist strap devices for lat pulldowns performed with 60 lbs, 90 lbs, 120 lbs, and 150 lbs of weights, respectively. These weights respectively represent the intensity levels of 40%, 60%, 80%, and 100%. The absolute value error sums in FIGS. 21, 22, 23, and 24 are 1392 BPM, 1959 BPM, 2078 BPM, and 3184 BPM, respectively. FIG. 25 shows a graph 2500 illustrating experimental data from the chest strap device for lat pulldowns performed at 40% (2502), 60% (2504), 80% (2506), and 100% (2508)

intensity. FIG. 26 shows a graph 2600 illustrating experimental data from the wrist strap device for lat pulldowns performed at 40% (2602), 60% (2604), 80% (2606), and 100% (2608) intensity. FIG. 27 shows a graph 2700 with a regression curve 2702 (dotted line) and a curve 2704 (solid line) that is created by plotting the error in the PPG-measured heart rate against the intensity level. The R-squared value is 0.89581.

Figure 32:
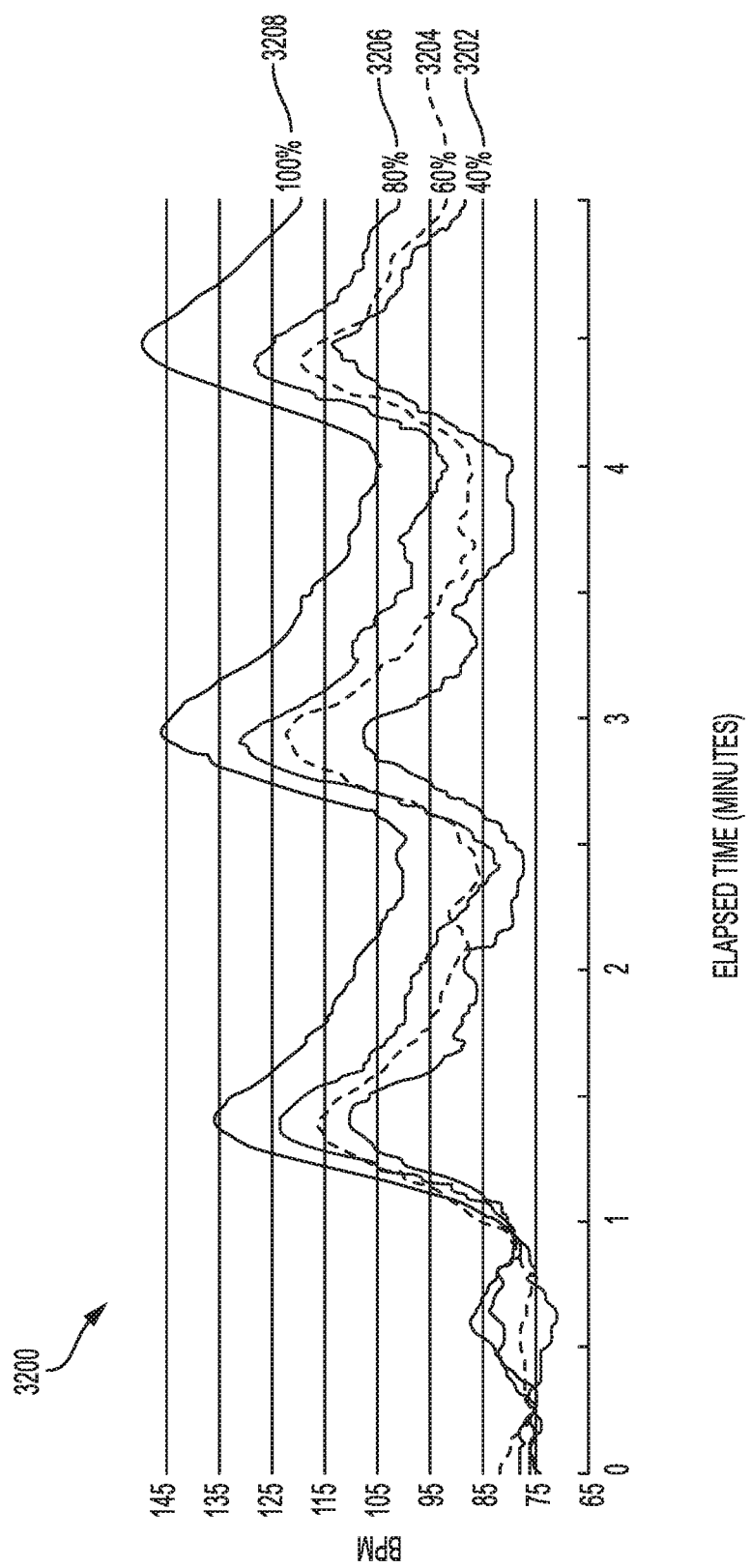
Figure 33:
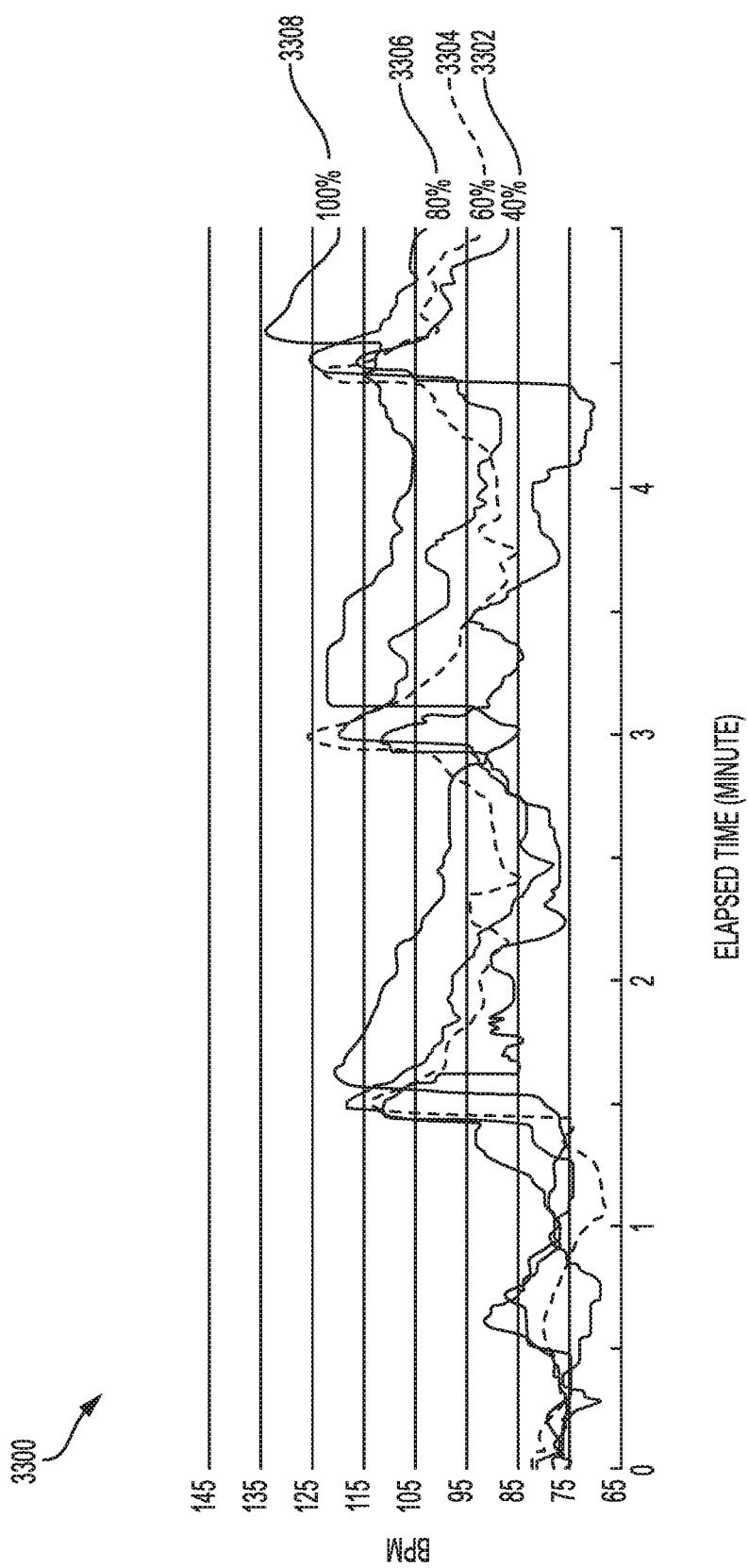
Figure 34:
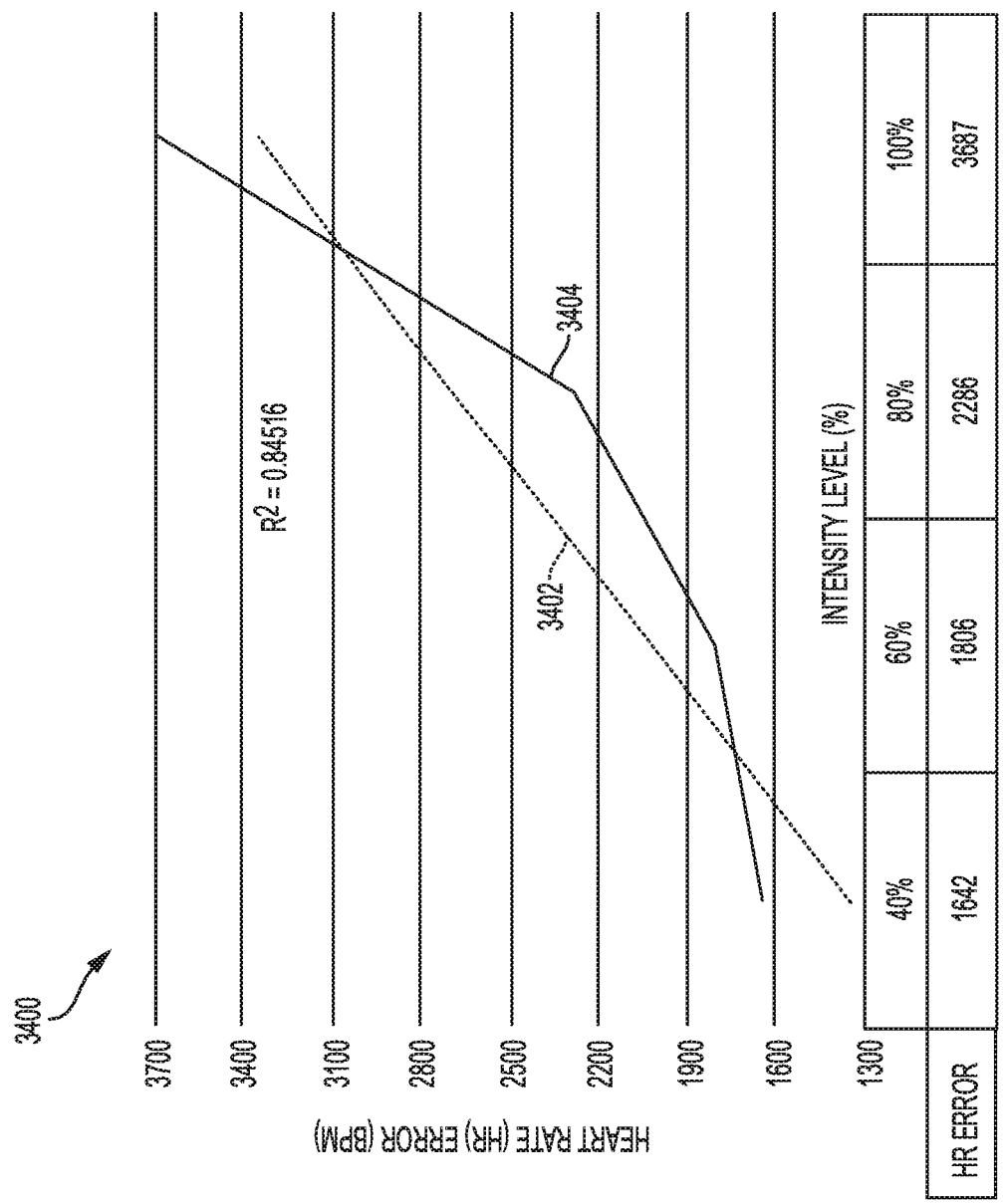

FIGS. 28, 29, 30, and 31 show experimental data from both the chest strap and wrist strap devices for dumbbell curls performed with 12.5 lbs, 18 lbs, 25 lbs, and 31 lbs of weights, respectively. These weights respectively represent the intensity levels of 40%, 60%, 80%, and 100%. The absolute value error sums in FIGS. 28, 29, 30, and 31 are 1642 BPM, 1806 BPM, 2286 BPM, and 3687 BPM, respectively. FIG. 32 shows a graph 3200 illustrating experimental data from the chest strap device for dumbbell curls performed at 40% (3202), 60% (3204), 80% (3206), and 100% (3208) intensity. FIG. 33 shows a graph 3300 illustrating experimental data from the wrist strap device for dumbbell curls performed at 40% (3302), 60% (3304), 80% (3306), and 100% (3308) intensity. FIG. 34 shows a graph 3400 with a regression curve 3402 (dotted line) and a curve 3404 (solid line) that is created by plotting the error in the PPG-measured heart rate against the intensity level. The R-squared value is 0.84516.

These and other experiments have shown that there is a correlation between the error in the PPG-measured heart rate and the intensity level at which the exercise is performed. This correlation varies between different types of exercises. Generally, as the intensity level increases, the error also increases. Also, as the intensity level decreases, the error also decreases. For example, a similar experiment with lat pulldowns as above was performed, except that the intensity level started at 100% and was decreased to 80%, then to 60%, and then to 40%. The results showed a direct correlation with an R-squared value of 0.94164.

A correlation between the error and the intensity level was also observed with exercises that did not require hand-grip pushing or pulling. For example, when barbell squats were performed, a direct correlation between the error in the PPG-measured heart rate and the intensity level was observed. It is believed that tension in the upper extremities also plays a factor along with hand grip and wrist movement.

Additional adjustments can be made to the data. For example, the data can be normalized for time under tension for each set. As another example, the error can be taken over the start of a set up to a specified time frame after completion of the set to ensure that PPG is captured within that timeframe. These example adjustments can significantly improve the correlation.

The above-described experimental data is provided for illustrative purposes only. Different kinds of experiments can be designed and performed to produce new or different data. For example, the following variables in the experiments can be changed: the traits of the person(s) subject to the experiments (e.g., age, gender, weight, height, skill level for the given exercise, medical history, current physical condition); the intensity levels; the number of intensity levels; the types of exercise; the number of sets; the number of reps; the duration of the exercise; the order, in which the exercise at different intensities is performed; the location; the exercise room temperature; the humidity level; and the time and date. In some cases, different data may result even if all the controllable variables are set to the same values because of the natural variability in human bodies.

In some embodiments, an intensity level as described in the present disclosure can be supplemented or replaced with other types of measures. For example, a level of efforts (e.g., amount of efforts applied) can be considered. In some embodiments, a level of efforts can be from maximal muscle contraction and/or muscular fatigue. In some embodiments, the ability to quantify efforts can increase efficacy of treatment of physical/occupational therapy and help with body weight training. This can further help with monitoring training adaptations to give user feedback to change the user's routine. The use of these other types of measures can apply not only to exercise but also to potential disease states where the physiological effort by change can be due to the disease. This can provide quantifiable information compared to perceived effort. This can also lead to understanding recovery as well as understanding how work or muscular exertion someone is applying. A foundation can be laid with analysis of the PPG error that can lead to characterizing the morphology of the error/estimate curves to many activities and many different populations.

While some of the data analyses in the present disclosure have been discussed in terms of drawing and using graphs, the visual representations of these graphs may not be necessary in implementing systems and methods for these analyses. For example, a system or method can use hardware and/or software to programmatically analyze heart rate related data without drawing any graph. Also, the graphs discussed in the present disclosure can be drawn using other forms, such as a line graph, bar graph, 2D graph, 3D graph, scatterplot, pictograph, pie graph, time series graph, stem and leaf plot, histogram, and dot plot.

It is to be understood that the present disclosure is not limited in its application to the details of construction and to the arrangements of the components set forth in the description or illustrated in the drawings. The present disclosure is capable of other embodiments and of being practiced and carried out in various ways. In addition, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the present disclosure. It is important, therefore, that the claims be regarded as including such equivalent constructions insofar as they do not depart from the spirit and scope of the present disclosure.

Although the present disclosure has been described and illustrated in the foregoing exemplary embodiments, it is understood that the present disclosure has been made only by way of example, and that numerous changes in the details of implementation of the present disclosure may be made without departing from the spirit and scope of the present disclosure, which is limited only by the claims which follow.

What is claimed is:

1. A method for improving an accuracy of a wearable device while calculating an intensity level of an exercise for a user, the method comprising:
    detecting, by one or more motion sensors of the wearable device, one or more body movements of the user;
    determining, by the processor circuit, at least one of a type of exercise that the user is performing or a skill level of the user based on the detected one or more body movements;
    measuring, by a heart rate sensor of the wearable device, a heart rate of the user, wherein the heart rate sensor comprises a photoplethysmogram (PPG) sensor and the PPG sensor is configured to be worn adjacent to the user's skin;

identifying, by the processor circuit, experimental data from a library of experimental data, wherein the identified experimental data is associated with a heart rate similar to the measured heart rate;

form, by the processor circuit, combination data using the measured heart rate and the identified experimental data to thereby improve the accuracy of the measured heart rate;

calculating, by the processor circuit, an intensity level of the exercise based on the type of exercise or the skill level and the combination data using the measured heart rate and the identified experimental data; and outputting, by the processor circuit, the determined intensity level of the exercise.

2. The method of claim 1, wherein the one or more motion sensors comprise at least one of an accelerometer, a gyroscope, or a magnetometer.

3. The method of claim 1, wherein outputting the determined intensity level of the exercise comprises:

providing, by the processor circuit, coaching information to the user based on at least one of the determined intensity level, the user's age, gender, experience level, activity level, physical condition, medical history, training history, or training goals.

4. The method of claim 1, wherein the library of experimental data comprises heart rates and exercise intensity levels associated with the heart rates.

5. The method of claim 4, wherein the library of experimental data further comprises at least one of ages, genders, physical conditions, medical history, weights, heights, body mass indexes, types of exercise, duration of exercise, fitness levels, experience levels, body temperatures, external temperatures, or external humidity levels.

6. The method of claim 1, wherein identifying the experimental data from the library of experimental data comprises:

comparing a first signature of the measured heart rate to a second signature of a heart rate associated with the experimental data from the library of experimental data.

7. The method of claim 6, wherein the first signature comprises a shape of a data curve.

8. A system for improving an accuracy of a wearable device while calculating an intensity level of an exercise for a user, the system comprising:

one or more motion sensors configured to detect one or more body movements of the user;

a heart rate sensor configured to measure a heart rate of the user, wherein the heart rate sensor comprises a photoplethysmogram (PPG) sensor and the PPG sensor is configured to be worn adjacent to the user's skin;

a processor circuit in communication with the one or more motion sensor and the heart rate sensor and configured to execute instructions causing the processor circuit to:

determine at least one of a type of exercise that the user is performing or a skill level of the user based on the detected one or more body movements;

compare the heart rate with a library of experimental data;

identify experimental data from a library of experimental data, wherein the identified experimental data is associated with a heart rate similar to the measured heart rate;

form combination data using the measured heart rate and the identified experimental data to thereby improve the accuracy of the measured heart rate;

calculate an intensity level of the exercise based on the type of exercise or the skill level and the combination data using the measured heart rate and the identified experimental data; and output the determined intensity level of the exercise.

9. The system of claim 8, wherein the one or more motion sensors comprise at least one of an accelerometer, a gyroscope, or a magnetometer.

10. The system of claim 8, wherein the instructions further cause the processor circuit to:

provide coaching information to the user based on at least one of the determined intensity level, the user's age, gender, experience level, activity level, physical condition, medical history, training history, or training goals.

11. The system of claim 8, wherein the library of experimental data comprises heart rates and exercise intensity levels associated to the heart rates.

12. The system of claim 11, wherein the library of experimental data further comprises at least one of ages, genders, physical conditions, medical history, weights, heights, body mass indexes, types of exercise, duration of exercise, fitness levels, experience levels, body temperatures, external temperatures, or external humidity levels.

13. A mobile device comprising the system of claim 8.

* * * * *